United States Patent [19]
Ruben et al.

[11] Patent Number: 5,642,734
[45] Date of Patent: Jul. 1, 1997

[54] METHOD AND APPARATUS FOR NONINVASIVELY DETERMINING HEMATOCRIT

[75] Inventors: Paul Ruben, Murray; Allan L. Kaminsky, Holladay, both of Utah

[73] Assignee: Microcor, Inc., Murray, Utah

[21] Appl. No.: 602,700

[22] Filed: Feb. 16, 1996

Related U.S. Application Data

[63] Continuation-in-part of Ser. No. 425,404, Apr. 20, 1995, Pat. No. 5,526,808, which is a continuation of Ser. No. 298,795, Aug. 31, 1994, abandoned, which is a continuation of Ser. No. 114,131, Aug. 30, 1993, abandoned, which is a continuation of Ser. No. 592,851, Oct. 4, 1990, abandoned.

[51] Int. Cl.$^6$ .................................................. A61B 5/00
[52] U.S. Cl. ............................................ 128/693; 128/734
[58] Field of Search ............................... 128/693, 694, 128/734; 364/413.02, 413.07

[56] References Cited

U.S. PATENT DOCUMENTS

| | | |
|---|---|---|
| 3,828,260 | 8/1974 | Underwood . |
| 3,835,839 | 9/1974 | Brown . |
| 3,835,840 | 9/1974 | Mount . |
| 3,871,359 | 3/1975 | Pacela . |
| 3,994,284 | 11/1976 | Voelker . |
| 4,047,205 | 9/1977 | Grosskopf . |
| 4,086,631 | 4/1978 | Vick . |
| 4,679,426 | 7/1987 | Fuller et al. . |
| 4,738,655 | 4/1988 | Brimhall et al. . |
| 4,765,179 | 8/1988 | Fuller et al. . |
| 4,835,477 | 5/1989 | Polaschegg et al. . |
| 4,887,458 | 12/1989 | Baker et al. . |
| 4,909,261 | 3/1990 | Rothenberg . |
| 5,040,538 | 8/1991 | Mortazavi . |
| 5,040,539 | 8/1991 | Schmitt et al. . |
| 5,101,825 | 4/1992 | Gravenstein et al. . |
| 5,203,344 | 4/1993 | Scheltinga et al. . |
| 5,246,002 | 9/1993 | Prosser . |
| 5,246,003 | 9/1993 | DeLonzor . |
| 5,277,181 | 1/1994 | Mendelson et al. . |
| 5,372,136 | 12/1994 | Steuer et al. . |
| 5,421,341 | 6/1995 | Marangoni . |
| 5,427,109 | 6/1995 | Frankenreiter . |
| 5,522,388 | 6/1996 | Ishikawa et al. ....................... 128/633 |

FOREIGN PATENT DOCUMENTS

| | | | |
|---|---|---|---|
| 83/03746 | 11/1983 | WIPO | ................................. 128/734 |

OTHER PUBLICATIONS deVries et al., "Implications of the dielectrical behaviour of human blood for continuous online measurement of haematocrit," Med. & Biol. Eng. & Comput., Sep. 1993, pp. 445–448.

(List continued on next page.)

Primary Examiner—Angela D. Sykes
Assistant Examiner—Eric F. Winakur
Attorney, Agent, or Firm—Trask, Britt & Rossa

[57] ABSTRACT

A method and apparatus for noninvasively determining hematocrit utilizing the frequency-dependent electrical impedance characteristics of whole blood by electrically stimulating a patient body portion containing a vascular compartment with a current source over a range of frequencies. A hematocrit measurement system includes a signal generator and demodulator (SGD) that sends an applied signal to an electrode pod that applies a current to a limb of a patient. The electrode pod receives resulting measured voltage signals and provides them to the SGD. The SGD provides to a personal computer (PC) signals indicative of the current passing through the limb of a patient and the resulting voltage. The voltage and current may be measured for various frequencies over, for example, a range from about 10 kHz to about 10 MHz. The electrical impedance from the blood alone is isolated from the total limb impedance from the blood, tissue, bone, etc. by determining the difference between measurements at different blood volumes. The hematocrit is determined by the PC based on inphase and quadrature data provided by the SGD. A neural network may be useful in determining the hematocrit from the blood impedance patterns.

85 Claims, 10 Drawing Sheets

OTHER PUBLICATIONS

Yamakoshi et al., "Noninvasive Measurement of Hematocrit by Electrical Admittance Plethysmography Technique," *IEEE Transactions on Biomedical Engineering*, vol. BME–27, No. 3, Mar. 1980, pp. 156–161.

Arenson et al., "Dual–channel self–balancing impedance plethysmograph for vascular studies," Med. & Biol. Eng. & Comput., Mar. 1981, 19, 157–164.

Visser et al., "Impedance Cardiography and Electrical Properties of Blood," Proceedings of the Vth ICEBI, Aug. 1981, Tokyo, pp. 13–16.

Meijer et al., "Differential impedance plethysmography for measuring thoracic impedances," Med. & Biol. Eng. & Comput., Mar. 1982, 20, 187–194.

Swanson et al., "Simple design for an impedance plethysmograph," Med. & Biol. Eng. & Comput., Jul. 1982, 20, 461–465.

Swanson et al., "Errors in four–electrode impedance plethysmography," Med. & Biol. Eng. & Comput., Nov. 1983, 21, 674–680.

Neelakantaswamy et al., "Conductimetric experiment to assay the haemoglobin content of blood," Med. & Biol. Eng. & Comput., Jul. 1984, 22, 367–370.

Goovaerts et al., "Microprocessor–based system for measurement of electrical impedances during haemodialysis and in postoperative care," Med. & Biol. Eng. & Comput., 1988, 26, 75–80.

Tremper et al., "Pulse Oximetry," Anesthesiology 70:98–108, Jan. 1989.

Meijer et al., "Measurement of transcellular fluid shift during haemodialysia," Med. & Biol. Eng. & Comput., Mar. 1989, 27, 147–158 (Parts 1 and 2).

Lozano et al., "Two–frequency impedance plethysmograph: real and imaginary parts," Med. & Biol. Eng. & Comput., Jan. 1990, 28, 38–42.

*EXAR Databook*, EXAR Corp., San Jose, Calif., 1987, pp. 6–62 through 65, and 11–68 through 71.

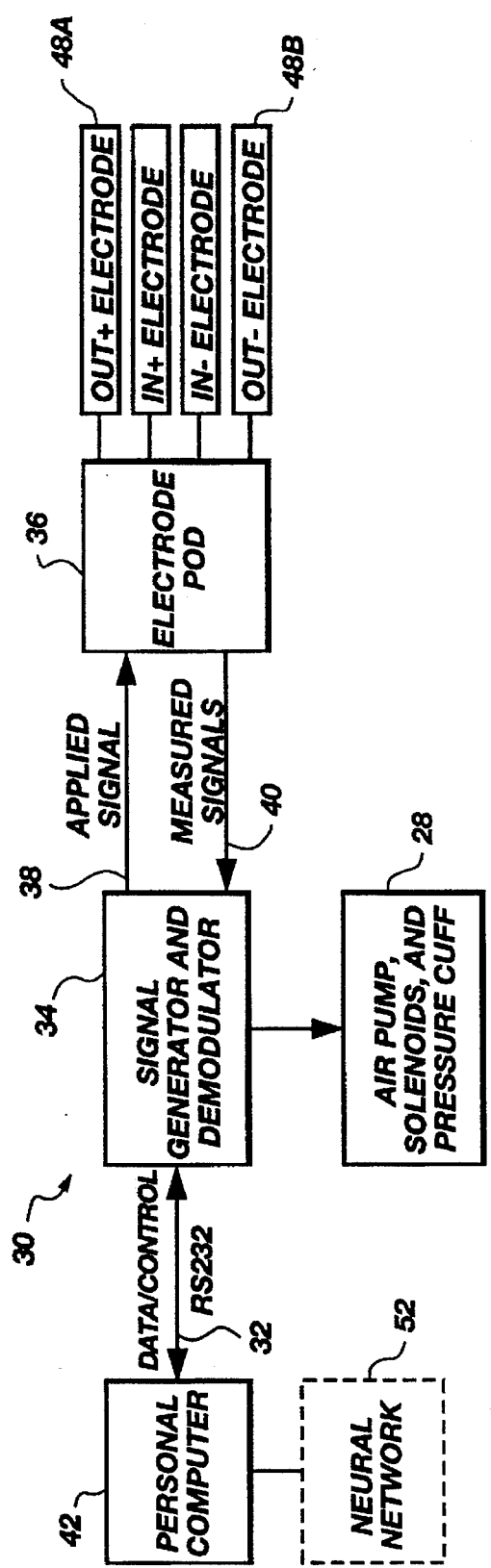
Fig. 4
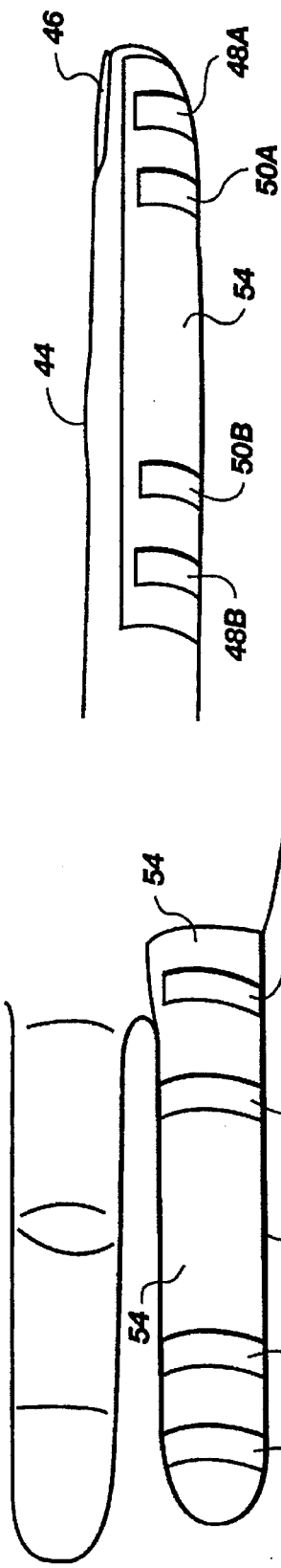
Fig. 5A
Fig. 5B

METHOD AND APPARATUS FOR NONINVASIVELY DETERMINING HEMATOCRIT

This application is a continuation-in-part of U.S. patent application Ser. No. 08/425,404 filed Apr. 20, 1995, now U.S. Pat. No. 5,526,808, which is a continuation of U.S. patent application Ser. No. 08/298,795 filed Aug. 31, 1994, abandoned, which is a continuation of U.S. patent application Ser. No. 08/114,131 filed Aug. 30, 1993, abandoned, which is a continuation of U.S. patent application Ser. No. 07/592,851 filed Oct. 4, 1990, abandoned.

BACKGROUND OF THE INVENTION

1. Field of the Invention

The present invention relates generally to determination of the Packed Cell Volume or relative volume percent of erythrocytes (red blood corpuscles), also known as the hematocrit, of whole blood, and more specifically to a method and apparatus for making such determination noninvasively through coherent techniques.

2. State of the Art

Hematocrit is traditionally obtained by acquiring a patient blood sample from a vein via a syringe, or by use of a capillary tube from a finger stick, or puncture. The blood, contained in an elongated vessel, is then centrifuged and the height percentage of the column of blood in the vessel which is solid represents the hematocrit.

More recently, hematocrit has been obtained by the use of elaborate and expensive cell counting laboratory instruments which are also used to provide differentiations of white blood cells, platelets, etc. However, as with the centrifuge method, the blood must be invasively removed from the patient for analysis.

In the course of routine medical procedures, such as the daily blood work performed in hospitals, the necessity of obtaining blood samples from patients and then centrifuging or otherwise analyzing the drawn blood presents no great inconvenience, as the volume of samples is large (warranting expensive automated equipment) and the time delay in obtaining results from a laboratory is generally acceptable. However, in catastrophic situations such as are encountered in the emergency rooms and shock trauma units, as well as in the course of surgical procedures wherein blood loss is probable, the hematocrit determination apparatus and methodology of the prior art are markedly deficient.

In the foregoing environments, there may be no time to draw blood, and in fact it may be impossible to identify a vein from which to draw it. Drawing blood intermittently during surgical procedures is inconvenient if not impractical, and analyzing periodic samples is time and labor intensive. Moreover, hematocrit may vary and drop at such an accelerated rate from unobserved blood loss that by the time the emergency or surgical personnel are belatedly made aware of a problem by laboratory personnel, the patient may be in acute difficulty or even deceased.

It has been proposed to measure hematocrit noninvasively, as noted in "Noninvasive Measurement of Hematocrit by Electrical Admittance Plethysmography Technique," *IEEE Transactions of Biomedical Engineering*, Vol. BME-27, No. 3, March 1980 pp. 156–161. However, the methodology described in the foregoing article involves submerging an extremity, such as a finger, in an electrolyte (NaCl solution) and varying the electrolyte concentration to compensate for pulsatile electrical admittance variations by matching the electrolyte resistivity to that of the blood in the extremity; the resistivity of the electrolyte is then determined in a resistivity cell, and converted to a hematocrit value via a nonlinear least-squares regression calibration curve generated by matching centrifuged hematocrit for various erythrocyte concentrations to resistivity data previously taken directly from blood resistivity measurements of the same specimens. Aside from being unwieldy to employ in an emergency or operating room environment, to the inventors' knowledge the technique as described in the referenced article has never been followed up or verified by further research, or employed in practice.

A measurement technique termed "impedance plethysmography," or using impedance techniques to obtain a waveform, is conceptually rooted in biomedical antiquity. Medical literature abounds with vascular studies, respiration studies and attempts to determine cardiac output (the actual volume of blood flowing from the heart) by impedance techniques. None of these techniques has been proven to work particularly well, although there have been attempts at commercial instruments based on the concept. A variant of impedance plethysmography, however, electrically models intracellular as well as extracellular tissue components and employs a comparison of measurements of tissue impedance responsive to applied electrical currents at two frequencies to quantify the intracellular and extracellular tissue components. While not directly related to the problem solved by the present invention, the electrical tissue model is useful to an understanding thereof.

In recent years, a technique known as pulse oximetry has been employed to measure blood oxygenation during induction of general anesthesia. While pulse oximetry does not provide a hematocrit indication, one may consider it helpful to an understanding of the method and apparatus of the present invention. Pulse oximetry relies upon the fact that the light absorbance of oxygenated hemoglobin and that of reduced hemoglobin differ at two wavelengths of light (generally red and near infrared) employed in an oximeter, and that the light absorbances at both frequencies have a pulsatile component which is attributable to the fluctuating volume of arterial blood in the patient body portion disposed between the light source and the detector of the oximeter. The pulsatile or AC absorbance response component attributable to pulsating arterial blood is determined for each wavelength, as is the baseline or DC component which represents the tissue bed absorbances, including venous blood, capillary blood, and nonpulsatile arterial blood. The AC components are then divided by their respective DC components to obtain an absorbance that is independent of the incident light intensity, and the results divided to produce a ratio which may be empirically related to $SaO_2$, or oxygen saturation of the patient's blood. An excellent discussion of pulse oximetry may be found in "Pulse Oximetry," by K. K. Tremper et al., *Anesthesiology*, Vol. 70, No. 1 (1989) pp. 98–108.

SUMMARY OF THE INVENTION

The present invention provides a method and apparatus for noninvasive hematocrit determination. In practicing the present invention, impedance of blood is measured via application of stimulation and sensor electrodes to a portion of the body that contains a vascular compartment of arteries, capillaries, and veins. For the sake of convenience, the electrodes are usually applied to a finger. The stimulation electrodes are driven with an alternating voltage over a range of frequencies.

In a preferred embodiment of the invention, the sensed voltage signals are amplified by a high input impedance voltage detector, converted to the digital domain by an analog-to-digital converter, and then demodulated via mixers into two complex waveforms, one representative of the stimulation current and another representative of the sense voltage at a selected frequency. The waveforms are processed by a microcomputer to determine the tissue impedance scan indicia. Then, the blood volume is altered and another tissue impedance scan is made. In a preferred embodiment, a pressure cuff is used to alter the blood volume. Two tissue scans, one at one blood volume and one at another blood volume, are used to determine a blood impedance scan. The impedance of the whole blood is separated from the total impedance through a parallel model. The whole blood impedance indicia is correlated to hematocrit by recognizing patterns in the blood impedance scan. It is also possible and contemplated as part of the invention to determine hematocrit using the preferred embodiment of the invention by analyzing the phase shift pattern with a neural network.

The invention for which protection is sought is defined in the claims as filed or later added or amended. If a limitation that is described or shown in the specification or drawings is not included in a claim, the claim should not be interpreted to include the limitation.

BRIEF DESCRIPTION OF THE DRAWINGS

The present invention will be more fully understood by one of ordinary skill in the art through a review of the following detailed description of the preferred embodiments in conjunction with the accompanying drawings, wherein:

FIG. 4 comprises a block diagram schematic of a preferred embodiment of a system of the present invention;

FIG. 5A comprises a bottom plan view of a limb to which electrodes are applied;

FIG. 5B comprises a side view of the limb of FIG. 5A;

DETAILED DESCRIPTION OF THE ILLUSTRATED EMBODIMENTS

A. Multi-Frequency Embodiments

1. Basic Electrical Models

Figure 1A:
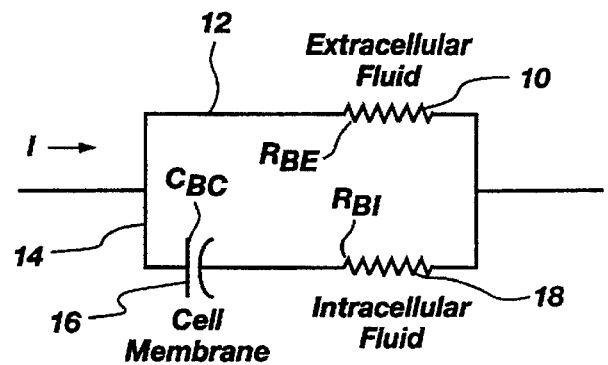
FIG. 1A comprises a circuit schematic for a first-order electrical model of whole blood in a large vessel.

FIG. 1A is an electrical circuit model that represents an approximation of the behavior of whole blood in a large vessel when subjected to an alternating electrical current I. Resistor 10 in circuit path 12 represents the resistance $R_{BE}$ of the extracellular or plasma component. A capacitor 16 and resistor 18 in a parallel circuit path 14 represent the capacitance $C_{BC}$ of the cell membrane and the resistance $R_{BI}$ of intercellular fluid of the erythrocyte or red blood corpuscles. At low frequencies (such as 50 kHz), the impedance of whole blood (e.g. that of both paths 12 and 14) is attributable primarily to the extracellular blood component circuit path 12, while at higher frequencies (for example, 1 MHz), the capacitive nature of the cell membrane of the red blood corpuscles results in a more significant impedance contribution from circuit path 14, reducing the magnitude of the whole blood impedance.

Figure 1B:
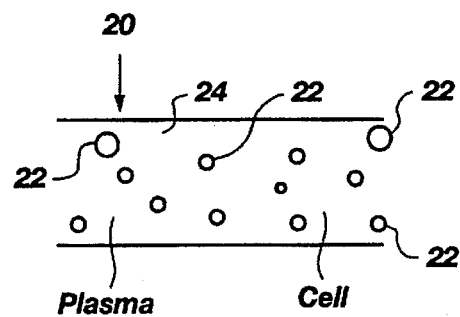
FIG. 1B comprises a schematic representation of fluid and membrane cells in a large vessel corresponding to the electrical model of FIG. 1A.

FIG. 1B illustrates a large vessel 20 containing many red blood cells 22 in plasma 24. As can be seen, there is a current path through plasma 24, even at low frequencies.

Figure 2A:
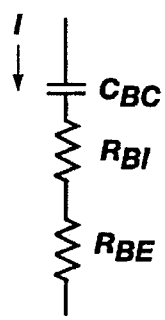
FIG. 2A comprises a circuit schematic for a first-order electrical model of whole blood in a small vessel.
Figure 2B:
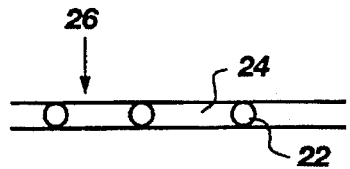
FIG. 2B comprises a schematic representation of fluid and membrane cells in a small vessel corresponding to the electrical model of FIG. 2A.

FIG. 2A is an electrical circuit model that represents an approximation of the behavior of whole blood in a small vessel when subjected to an alternating electrical current I. FIG. 2B illustrates a small vessel 26 in which cells 22 are about as wide as vessel 26 preventing a plasma path between cells 22 and the wall of vessel 26. In such a case, the path for current I is through a capacitance $C_{BC}$, in series with resistances $R_{BI}$ and $R_{BE}$. Accordingly, the impedance of and the amount of current flowing through vessel 26 changes as the frequency of current I increases. While the ratio of small vessels to large vessels is not known, it is believed that the effect of small vessels may be significant in the overall limb impedance. (There are some vessels that are slightly or somewhat larger than a small vessel and allow a small path around the cells.)

It is understood that in the circuits of FIGS. 1A and 2A, the maximum phase shift in impedance occurs when the frequency of current I is $f=1/(R_S C_{BC} 2\pi)$, where $R_S$ is $R_{BI}$ in the case of large vessels and $R_S$ is $R_{BI}+R_{BE}$ in the case of small vessels. It has been found that the maximum phase shift of blood occurs at about 1.6 MHz in large vessels. As described below, that maximum phase shift is used in determining the hematocrit. The large vessel model predominates in the blood impedance measurements. However, it is believed that the contribution of small vessels should not be ignored and that the maximum phase shift of the small vessels will occur at below 1.6 MHz. It is believed that the effect of the small vessels is reflected in the values throughout the spectrum.

However, when current is passed through a limb, such as is described below, the current passes not only through blood, but also through tissue, bone, etc. The impedance of the blood may be separated from the total limb impedance through a procedure described below. In brief, in FIG. 3A, the impedance $Z_U$ represents the total limb impedance when blood flow through the limb is unrestricted. In FIG. 3B, the blood flow through the limb is restricted and $Z_B$ represents the impedance of the additional blood accumulated as a result of the restriction. The total limb impedance during the restricted state is $Z_R$. The total impedance $Z_U$ and $Z_R$ may be calculated, and $Z_B = (Z_U \times Z_R)/(Z_U - Z_R)$. Therefore, the contribution of portions of the limb other than the blood does not have to be determined.

2. System Overview

Referring to FIG. 4, a hematocrit measurement system 30 includes a signal generator and demodulator (SGD) 34 that sends a signal to an electrode pod 36 through conductor 38 and receives measured signals from electrode pod 36 through conductor 40. SGD 34 provides to a personal computer (PC) 42, through conductors 32 and an RS-232 port, signals indicative of the current passing through the limb of a patient and the resulting voltage. The voltage and current may be measured for various frequencies over, for example, a range from 10 kHz to 10 MHz.

The impedance from the blood alone is isolated from the total limb impedance from the blood, muscle, bone, etc. by measuring the limb impedance of different blood volumes. As described below, an air pump, solenoid(s), and pressure cuff 28 may be used to cause a change in blood volume in the limb.

PC 42 determines the hematocrit. The hematocrit may be determined from the signals from SGD 34 alone, or in combination with various other data regarding the particular patient such as age, sex, weight, temperature, illnesses, etc., or regarding patients in general. In this regard, as described below, a neural network may be useful. A neural network may be executed in PC 42 or in a separate computer 52, shown in dashed lines.

3. Electrode Pod and Electrodes

Referring to FIGS. 4 and 5A and 5B, electrode pod 36 provides an alternating electrical current signal to a limb 44 (such as a finger having a finger nail 46) of a patient through electrodes 48A and 48B. (FIG. 5A shows the underside of the two fingers next to the thumb of a left hand.) The resulting voltage drop across limb 44 is measured through electrodes 50A and 50B. The voltage between electrodes 48A and 48B may be about three volts. Electrodes 48A, 48B, 50A, and 50B may be standard, commercially available electrodes.

Electrodes 48A, 48B, 50A, and 50B may be conveniently held in place through a piece of tape 54 that covers both the electrodes and a portion of limb 44. However, tape 54 preferably does not restrict blood flow. Tape 54 may extend ½ to ¾ around the circumference of limb 44. In addition to holding the electrodes in place, tape 54 stiffens limb 44, which makes the measurement procedures more controlled. A splint or mylar may also be used.

Figure 6:
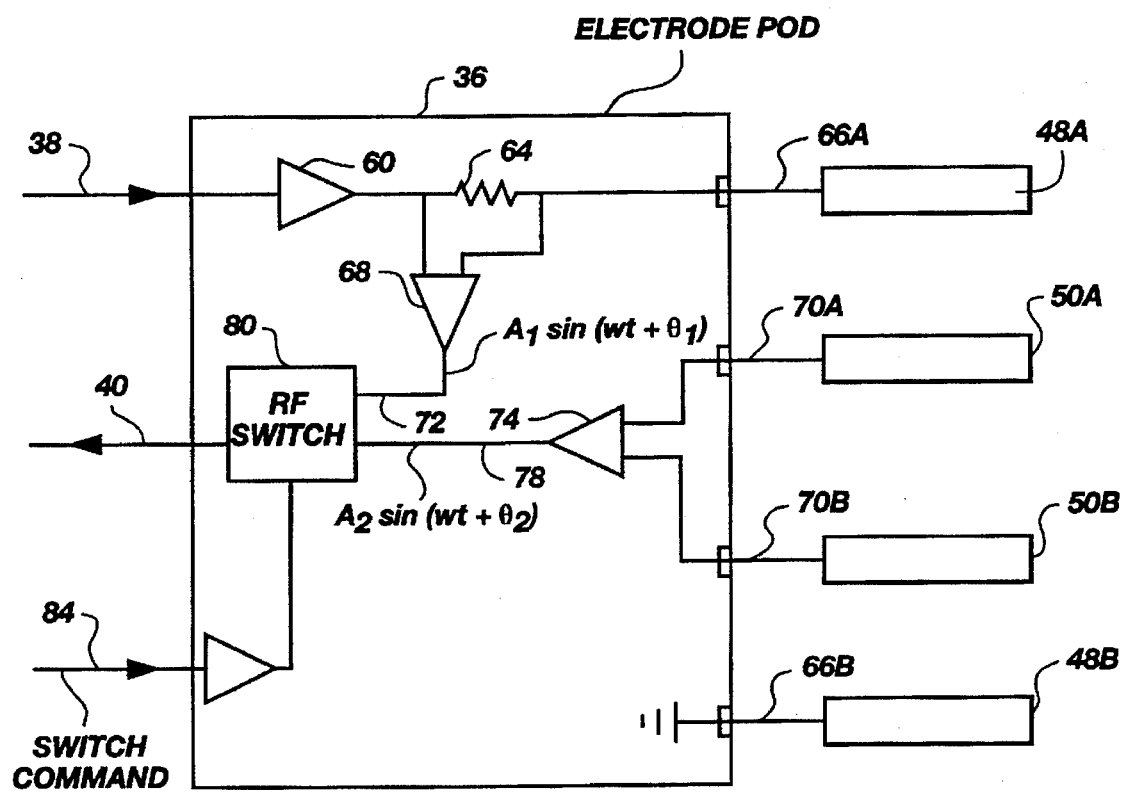
FIG. 6 comprises a more detailed block diagram schematic of the electrode pod of the system of FIG. 4.

Referring to FIG. 6, electrode pod 36 includes a 50 ohm termination buffer 60 that receives a sine signal having frequency $\omega$ on conductor 38 from SGD 34. A sense resistor 64 is connected in series between buffer 60 and a conductor 66A, to which electrode 48A is connected.

Figure 7:
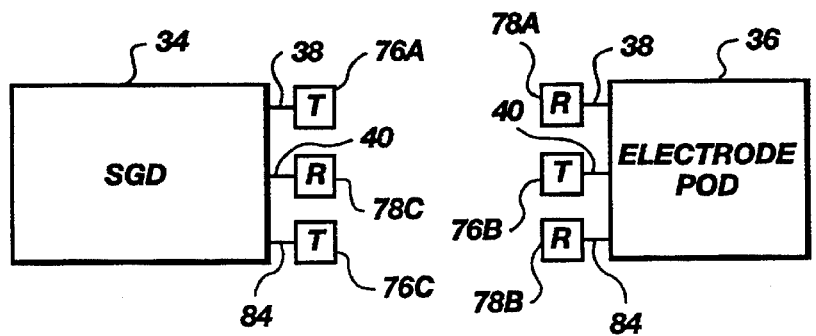
FIG. 7 comprises a schematic representation of a wireless version of the signal generator and demodulator and electrode pod of FIG. 4.

Electrodes 48A, 48B, 50A, and 50B are connected to electrode pod 36 through conductors 66A, 66B, 70A, and 70B, which are preferably as short as possible. Alternatively, wireless communication could be used as shown in FIG. 7, which includes transmitters 76A, 76B, and 76C, and receivers 78A, 78B, and 78C. Wireless communication may be particularly useful in an operating room environment.

Referring again to FIG. 6, an instrumentation amplifier 68 provides to conductor 72 a signal $A_1 \sin(\omega t + \theta_1)$ indicative of the voltage drop across resistor 64, where "$A_1$" is the amplitude, and $\theta_1$ is a phase difference with respect to an original signal $\sin \omega t$, described below. Instrumentation amplifier 68 provides a high input impedance, and rejects the common mode voltage at conductor 66A while amplifying the voltage drop across resistor 64. Instrumentation amplifier 68 may comprise three operational amplifiers in a well known configuration.

An instrumentation amplifier 74 provides to a conductor 78 a signal $A_2 \sin(\omega t + \theta_2)$ that is indicative of the voltage between electrodes 50A and 50B, where "$A_2$" is the amplitude, and $\theta_2$ is a phase with respect to the original signal, $\sin \omega t$. The difference in phase between $\theta_1$ and $\theta_2$ is caused by the electrical capacitance in limb 44 between electrodes 48A and 50B, and differences in the speed and phase response of the instrumentation amplifiers 68 and 74. Accordingly, instrumentation amplifiers 68 and 74 should be chosen and constructed to minimize differences in their phase responses. The differences in speed and phase response of amplifiers 68 and 74 are calibrated out of the equipment using a dummy load. Thereafter, PC 42 stores the calibration information and subtracts out any differences.

Instrumentation amplifier 74 rejects the common mode voltage between conductors 66B and 70B and amplifies the differential voltage between conductors 70A and 70B. Instrumentation amplifier 74 may comprise three operational amplifiers in a well known configuration.

An RF switch 80 passes either the signal on conductor 72 or the signal on conductor 78 to conductor 40, under the control of a signal on conductor 84. RF switch 80 may switch at a rate of 110 (=2×55) times per second.

4. Signal Generator and Demodulator (SGD)

Figure 8:
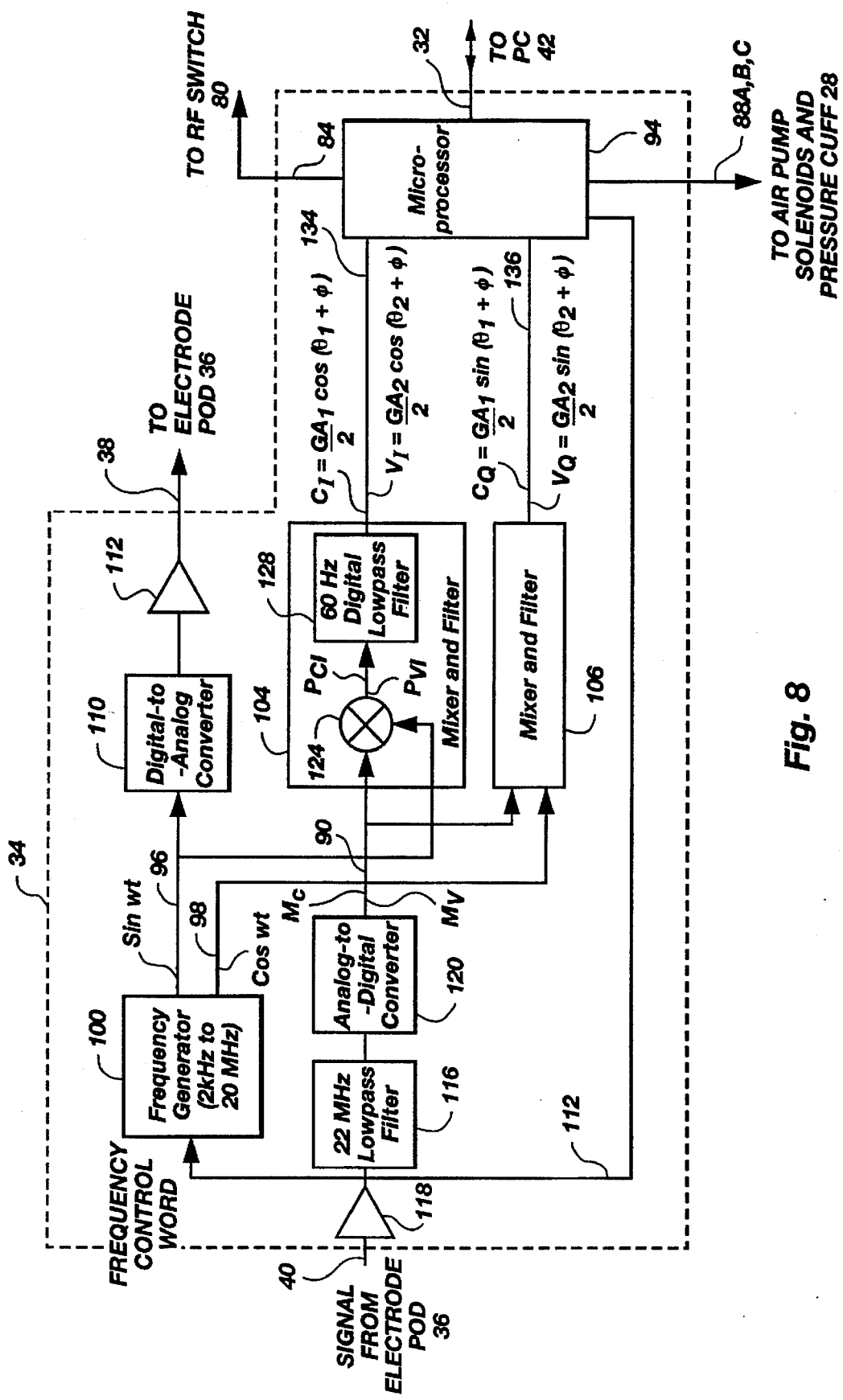
FIG. 8 comprises a more detailed block diagram schematic of the signal generator and demodulator of FIG. 4.

Referring to FIG. 8, SGD 34 produces the signal on conductor 38 and demodulates and filters the signals on conductor 40. SGD 34 may include a microprocessor 94 with an embedded EPROM, such as an HC6805. Microprocessor 94 provides control signals to the various components of SGD 34 to RF switch 80 through conductor 84, and to solenoids of air pump, solenoids, and pressure cuff 28, through conductors 88A, 88B, and 88C, as described in connection with FIG. 9, below. Microprocessor 94 also communicates with PC 42 through conductors 32.

A frequency generator 100 produces a digital sine signal $FG_{SIN}$ shown in equation (1) below to conductors 96:

$$FG_{SIN} = \sin \omega t \qquad (1),$$

where the amplitude is assumed to be unitary. From conductors 96, the signal $\sin \omega t$ is provided to mixer and filter 104, and to a DAC 110. The analog sine signal from DAC 110 is provided through a buffer 112 to conductor 38. The frequency of $FG_{SIN}$ is controlled by a frequency control word provided by PC 42 to frequency generator 100.

Frequency generator 100 also produces a digital cosine signal $FG_{COS}$ shown in equation (2) below, to conductors 98:

$$FG_{cos} = \cos\omega t \qquad (2),$$

where the amplitude is assumed to be unitary. Of course, $\cos\omega t$ is 90 degrees out of phase with $\sin\omega t$. From conductors 98, the signal $\cos\omega t$ is provided to mixer and filter 106.

The signals from electrode pod 36 on conductor 40 are received by a low pass filter 116 through a buffer 118. Low pass filter 116 removes harmonic frequency components or aliasing. The 22 MHz value was chosen to allow tissue impedance measurements with a $\sin\omega t$ at as high as 20 MHz. However, the analog electronics may have difficulties maintaining the required phase tolerance above about 10 MHz. With the 10 MHz upper limit, low pass filter 116 may have a lower cut off frequency. The filtered signals from low pass filter 116 are converted to digital signals through ADC 120, from which they are passed to mixers and filters 104 and 106.

DAC 110, ADC 120, and frequency generator 100 may be clocked at 60 MHz. However, if the maximum frequency of $\sin\omega t$ generated by frequency generator 100 is 10 MHz, then DAC 110, ADC 120, and frequency generator 100 may be clocked at, for example, 30 MHz.

Measured current indicating signals $M_c$ are provided by ADC 120 to conductors 90. Signals $M_c$ originate from conductor 72 in FIG. 6 and are processed through RF switch 80, buffer 118, low pass filter 116, and ADC 120. Signals $M_c$ are shown in equation (3), below:

$$M_c = G A_1 \sin(\omega t + \theta_1 + \phi) \qquad (3),$$

where $A_1$ and $\theta_1$ are the amplitude and phase of the signal at conductor 72, and $G$ and $\phi$ are the gain and phase shift caused by buffer 118, low pass filter 116, and ADC 120.

Measured voltage indicating signals $M_V$ are also provided by ADC 120 to conductors 90. Signals $M_V$ originate from conductor 78 in FIG. 6 and are processed through RF switch 80, buffer 118, low pass filter 116, and ADC 120. Signals $M_V$ are shown in equation (4), below:

$$M_V = G A_2 \sin(\omega t + \theta_2 + \phi) \qquad (4),$$

where $A_2$ and $\theta_2$ are the amplitude and phase of the signal at conductor 78, and $G$ and $\phi$ are the gain and phase shift caused by buffer 118, low pass filter 116, and ADC 120. Of course, signals $M_c$ and $M_V$ are merely examples of current indicating signals and voltage indicating signals, and other circuitry than is illustrated may be used to produce suitable current and voltage indicating signals.

In mixer and filter 104, a multiplier 124 multiplies $\sin\omega t$ on conductors 96 with the output of ADC 120. When RF switch 80 passes the signal on conductor 72, the output of multiplier 124 is the product $P_{CI}$ (current inphase), shown in equation (5), below:

$$\begin{aligned} P_{CI} &= G A_1 \sin(\omega t + \theta_1 + \phi) \times \sin\omega t \qquad (5) \\ &= ((G A_1/2)\cos(\theta_1 + \phi)) - ((G A_1/2)\sin(2\omega t + \theta_1 + \phi)), \end{aligned}$$

where $G$, $A_1$, $\theta_1$, and $\phi$ are defined in connection with equation (3). Mixer and filter 104 is illustrative of mixer and filter 106.

A 60 Hz digital lowpass filter 128 filters out the $((G A_1/2) \sin(2\omega t + \theta_1 + \phi))$ component as well as various noise, leaving only the DC component, $((G A_1/2) \cos(\theta_1 + \phi))$. The signal $((G A_1/2) \cos(\theta_1 + \phi))$ is applied to conductors 134 and is referred to as $C_I$, where "C" represents the current between electrodes 48A and 48B, and "I" stands for "in phase." Digital lowpass filter 128 may be constructed of multipliers and adders performing convolution in a well known manner.

When RF switch 80 passes the signal on conductor 78, the output of multiplier 124 is the product $P_{VI}$ (voltage inphase), shown in equation (6), below:

$$\begin{aligned} P_{VI} &= G A_2 \sin(\omega t + \theta_2 + \phi) \times \sin\omega t \qquad (6) \\ &= ((G A_2/2)\cos(\theta_2 + \phi)) - ((G A_2/2)\sin(2\omega t + \theta_2 + \phi)), \end{aligned}$$

where $G$, $A_2$, $\theta_2$, and $\phi$ are defined in connection with equation (4).

60 Hz digital lowpass filter 128 filters out the $((G A_2/2) \sin(2\omega t + \theta_2 + \phi))$ component as well as various noise, leaving only the DC component, $((G A_2/2) \cos(\theta_2 + \phi))$. The signal $((G A_2/2) \cos(\theta_2 + \phi))$ is applied to conductors 134 and is referred to as $V_I$, where "V" represents the current between electrodes 50A and 50B, and "I" stands for "in phase."

Mixing an original and modified signal to obtain amplitude and phase information is a "coherent" technique.

In mixer and filter 106, a multiplier (not shown) multiplies $\cos\omega t$ on conductors 98 with the output of ADC 120. When RF switch 80 passes the signal on conductor 72, the output of multiplier 124 is the product $P_{CQ}$ (current quadrature), shown in equation (7), below:

$$\begin{aligned} P_{CQ} &= G A_1 \sin(\omega t + \theta_1 + \phi) \times \cos\omega t \qquad (7) \\ &= ((G A_1/2)\sin(\theta_1 + \phi)) + ((G A_1/2)\sin(2\omega t + \theta_1 + \phi)), \end{aligned}$$

where $G$, $A_1$, $\theta_1$, and $\phi$ are defined in connection with equation (3). Note that the term "quadrature" derives from the cosine signal being 90 degrees out of phase with the sine signal.

A 60 Hz digital lowpass filter 128 filters out the $((G A_1/2) \sin(2\omega t + \theta_1 + \phi))$ component as well as various noise, leaving only the DC component, $((G A_1/2) \sin(\theta_1 + \phi))$. The signal $((G A_1/2) \sin(\theta_1 + \phi))$ is applied to conductors 136 and is referred to as $C_Q$, where "C" represents the current between electrodes 48A and 48B, and "Q" stands for "quadrature."

When RF switch 80 passes the signal on conductor 78, the output of multiplier 124 is the product $P_{VQ}$ (voltage quadrature), shown in equation (8), below:

$$\begin{aligned} P_{VQ} &= G A_2 \sin(\omega t + \theta_2 + \phi) \times \sin\omega t \qquad (8) \\ &= ((G A_2/2)\cos(\theta_2 + \phi)) - ((G A_2/2)\sin(2\omega t + \theta_2 + \phi)), \end{aligned}$$

where $G$, $A_2$, $\theta_2$, and $\phi$ are defined in connection with equation (4).

60 Hz digital lowpass filter 128 filters out the $((G A_2/2) \sin(2\omega t + \theta_2 + \phi))$ component as well as various noise, leaving only the DC component, $((G A_2/2) \sin(\theta_2 + \phi))$. The signal $((G A_2/2) \sin(\theta_2 + \phi))$ is applied to conductors 136 and is referred to as $V_Q$, where "V" represents the voltage between electrodes 50A and 50B, and "Q" stands for "quadrature."

Signals $C_I$ and $C_Q$ provide information regarding the amplitude and phase of the current between electrodes 48A and 48B. Signals $V_I$ and $V_Q$ provide information regarding the amplitude and phase of the voltage electrodes 50A and 50B. Signals V and C are complex (i.e., they have inphase components $V_I$ and $C_I$ and quadrature components $V_Q$ and $C_Q$).

The inphase and quadrature impedance waveforms $V_I$, $V_Q$, $C_I$, and $C_Q$ are sent to a computer, such as PC 42 where the complex impedance may be calculated at a 55 sample/second rate.

5. Computations in the PC

The signals $V_I$, $V_Q$, $C_I$, and $C_Q$ may be analyzed as follows.

The magnitude $C_{MAG}$ of the current components is determined through equation (9), below:

$$C_{MAG}=(C_I^2+C_Q^2)^{1/2} \quad (9),$$

where $C_I$ and $C_Q$ are the signals on conductors 134 and 136 from mixers and filters 104 and 106.

The phase $C_\phi$ of the current components is determined through equation (10), below:

$$C_\phi=\tan^{-1}(C_Q/C_I) \quad (10).$$

The magnitude $V_{MAG}$ of the voltage components is determined through equation (11), below:

$$V_{MAG}=(V_I^2+V_Q^2)^{1/2} \quad (11),$$

where $V_I$ and $V_Q$ are the signals on conductors 134 and 136 from mixers and filters 104 and 106.

The phase $V_\phi$ of the voltage components is determined through equation (12), below:

$$V_\phi=\tan^{-1}(V_Q/V_I) \quad (12).$$

The impedance Z is the ratio of complex numbers V and C.

The magnitude $Z_{MAG}$ component of the impedance is determined through equation (13), below:

$$Z_{MAG}=V_{MAG}/C_{MAG}=GA_2/GA_1=A_2/A_1 \quad (13),$$

where $V_{MAG}$ and $C_{MAG}$ are determined according to equations (11) and (9).

The phase component of the impedance is determined through equation (14), below:

$$Z_\phi=V_\phi-C_\phi=(\theta_2+\phi)-(\theta_1+\phi)=(\theta_2-\theta_1) \quad (14),$$

where $V_\phi$ and $C_\phi$ are determined according to equations (12) and (10).

The impedance from the blood alone is isolated from the total impedance from the blood, tissue, bone, etc. This isolation may be performed as follows. At each frequency in a scan, the limb impedance is determined by calculating $V_I$, $V_Q$, $C_I$, and $C_Q$ when blood flow through limb 44 is unrestricted and, therefore, the limb has a normal or unrestricted blood volume. Then, another scan is performed over the same frequencies when blood flow through limb 44 is restricted and, therefore, the limb has a restricted blood volume (which may be higher or lower than the unrestricted blood volume). Methods of restriction are discussed below.

Figure 3A:
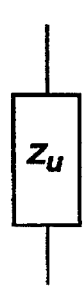
FIG. 3A shows a representation of the total impedance in a limb at a low blood volume.
Figure 3B:
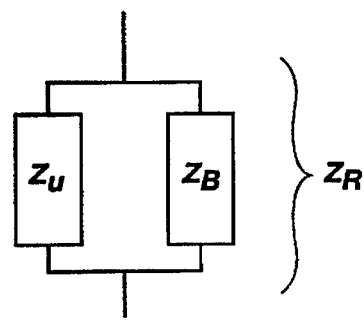
FIG. 3B shows a representation of the total impedance in a limb at high blood volume.

FIGS. 3A and 3B illustrate the situation in which restriction causes an increase in blood volume. The total limb impedance at lower blood volume when the limb is unrestricted is $Z_U$, illustrated in FIG. 3A. The total limb impedance at higher blood volume when the limb is restricted is $Z_R$, illustrated in FIG. 3B. Impedance $Z_R$ is the equivalent to impedance $Z_U$ in parallel with the impedance $Z_B$, where $Z_B$ is the blood present at higher volume that is not present at lower volume. (This model assumes that the extra blood has the same hematocrit as all other blood passing through the limb.) Impedance $Z_R$ is calculated through equation (15), below:

$$Z_R=(Z_B \times Z_U)/(Z_B+Z_U) \quad (15).$$

Both $Z_R$ and $Z_U$ can be measured and from them $Z_B$ can be computed. Solving for impedance $Z_B$ in equation (15) yields equation (16), below:

$$Z_B=(Z_U \times Z_R)/(Z_U-Z_R) \quad (16),$$

for the case in which restriction causes an increase in blood volume.

In the case in which restriction causes a decrease in blood volume, $Z_U$ is equivalent to $Z_R$ in parallel with $Z_B$, where $Z_B$ is the blood present at higher volume that is not present at lower volume. Then, impedance $Z_R$ is calculated through equation (17), below:

$$Z_U=(Z_B \times Z_R)/(Z_B+Z_R) \quad (17).$$

Both $Z_R$ and $Z_U$ can be measured and from them $Z_B$ can be computed. Solving for impedance $Z_B$ in equation (17) yields equation (18), below:

$$Z_B=(Z_U \times Z_R)/(Z_R-Z_U) \quad (18),$$

for the case in which restriction causes a decrease in blood volume.

Although blood impedance $Z_B$ includes both a magnitude and phase, the phase appears to be the stronger indicator of hematocrit. However, both phase and magnitude of $Z_B$ may be used in pattern analysis in a neural network.

The processes of determining $Z_B$ are repeated for various frequencies over a range from about 10 kHz to about 10 MHz. Various steps may be used. In the current embodiment, there may be from 3 steps per octave to 10 steps per octave, where octaves are 10 kHz, 20 kHz, 40 kHz, 80 kHz, 160 kHz, etc.

There are advantages and disadvantages in having a large versus a small number of steps. A large number of steps may be used to average out arterial pulsation noise, but takes more time and, therefore, there is a greater risk that the blood volume will undesirably and unpredictably change over time with a longer measurement.

It has been found by the inventors that the phase change increases (as a negative number) from about 10 kHz to in the region of 1.6 MHz and then begins to decrease (although there may be an inflection point at well below 1.6 MHz). (de Vries, P. M. J. M., et al., "Implications of the dielectrical behavior of human blood for continuous on-line measurement of hematocrit", *Med. Biol. Eng. & Comput.* 31, 445–448 (1993) notes a 1.6 MHz maximum phase.) However, it is expected that the maximum phase change will vary, depending on various factors. Therefore, a neural network approach is proposed.

6. Preferred Procedures

The following procedures may be used. A "scan" refers to the process of applying signals of various frequencies in steps between a lower and upper frequency limit to electrode 48A. As described above, this creates a current between electrodes 48A and 48B, and a voltage between electrodes 50A and 50B. It takes about one 55th of a second to gather $V_I$, $V_Q$, $C_I$, and $C_Q$ signals at each frequency. Digital filter 128 requires about 9 milliseconds to achieve the desired 60 Hz bandwidth. Accordingly, digital filter 128 processes $P_{CI}$ for 9 milliseconds and then processes $P_{VI}$ for 9 milliseconds at one frequency. The processes is then repeated for 9 milliseconds for $P_{CI}$ and then 9 milliseconds for $P_{VI}$ at another frequency. The corresponding digital filter in mixer and filter 106 similarly processes $P_{CQ}$ and $P_{VQ}$.

In a preferred embodiment, the software is written so that the lower and upper frequency limits are 10 kHz and 10 MHz, and the number of steps between the lower and upper limits are between 11 and 101 frequencies. If 101 frequencies are chosen, it takes about 1.8 seconds (=101/55) to complete a scan.

A "repetition" refers to the number of "scans" that are performed in quick succession before changing the blood volume. In a preferred embodiment, the software is written so there may be between 1 and 10 repetitions. The reason to perform multiple repetitions is as follows. Arterial pulsations cause a small alternating fluctuation in blood volume. The pulsations can affect the phase. If multiple repetitions are made, the variations in phase caused by arterial pulsations can be averaged and the effect reduced.

A "measurement" refers to the completion of a specified number of scan repetitions at a particular blood volume. In a preferred embodiment, the software is written to make any number of measurements up to 25. For example, a first measurement is at unrestricted blood volume. A second measurement is at restricted blood volume. A third measurement may be at the unrestricted blood volume or some other blood volume, and so forth. Depending on the restrictive pressure (such as from a cuff) and the vascular circulation, it can take between about 10 to 45 seconds for blood volume of limb 44 to reach a new equilibrium after the restrictive pressure is changed.

It is desirable to not make more measurements than is necessary in order to reduce the test time. A greater number of scans per measurement evens out pulsatile variations. It has been found that measurements yield different results, even taken at near the same time. Therefore, enough measurements should be made to ensure adequate results. Multiple cycles may be needed to produce satisfactory results. If the first few measurements give results with a small standard deviation, it may not be necessary to finish all the measurements.

There are various tradeoffs in the choice of values. For example, a large change in blood volume is desirable to produce a high signal to noise ratio with respect to arterial pulsations. However, a large blood volume change takes a longer time and causes more capillary beds to open up to accommodate additional blood volume.

Of course, the various values and limits for frequencies, steps, scans, repetitions, and cycles can be changed through altering the software.

7. A Neural Network Approach

A neural network may analyze very complex, noisy data and find patterns (or combinations of data) that can be used to determine underlying parameters. These patterns are usually not apparent to human observers. In a statistical sense, neural networks are capable of performing non-linear non-parametric regression.

Finding neural network solutions to complex data analysis problems may be as much art as science. There are many different neural network paradigms, and each of these paradigms uses the specification of a number of critical parameters. These choices require a certain amount of experience, trial-and-error, etc. The search for a systematic neural network design approach is a very active area of research within the field of Artificial Intelligence.

The particular paradigms of interest in the present invention are believed to be those that produce continuous-valued outputs and that undergo supervised training. This is a technique of shaping the neural network in which the network is repeatedly exposed to both the data and the right answer. This allows the net to structure itself internally so that it extracts the features in the data that we have identified as being important to the present invention.

Clinical data collection could be gathered from several runs on each patient or subject. The runs could be performed with certain varying conditions (such as different height of the limb under test, applied heat to the limb, etc.). Thereby, several different environments could be produced with different patterns of data for the same hematocrit. In addition, blood could be drawn to accurately determine the actual hematocrit using the "gold standard" technique of centrifuging capillary tubes containing the subject's whole blood.

By collecting this diverse data on each subject and having a sufficient number of subjects, the neural nets will be trained to determine the underlying parameter of hematocrit.

Neural network 52 may be in PC 42 or an adjacent PC or other computer. Accordingly, in FIG. 4, neural network 52 is shown in dashed lines.

The following parameters could be considered by the neural network. With respect to the impedance waveforms, the neural network could consider parameters including frequency, magnitude, phase, and derivations thereof. With respect to the patient or subject, the neural network could consider parameters including the patient's age, weight, sex, temperature, illness, heat applied to the limb, blood pressure, and arm elevation and position. Of course, it is not necessary that the neural network consider each of these parameters.

Of course, the neural network would also consider the hematocrit measurements from centrifuging capillary tubes corresponding to the patient from which the other factors were obtained.

The neural network is used in two manners. First, it is used to derive a group of patterns and/or other data from a large amount of the parameters regarding patients and waveforms. Second, once the patterns and/or other data are derived, the neural network is used in determining the hematocrit of a particular patient (who, for example, may be on an operating table) by comparing patient and waveform data of the particular patient with the previously derived patterns and/or other data.

At present, it is believed that the neural network is able to process out the small vessel effect and produce the hematocrit value due to blood contained in large vessels.

As used herein, the term "patient" includes both those persons from whom the data is originally obtained to create the group of patterns or data, and those persons whose hematocrit is later determined from the group of patterns or data.

Look up tables may be used, although it is expected that many of the patterns (such as equations) may be too complicated to make look-up tables practical for most purposes.

8. Air Pump, Solenoid(s), and Pressure Cuff 28

There are various methods of changing the blood volume. For example, if limb 44 is a finger, blood volume may be changed through venous restriction about the upper arm of the patient, or arterial occlusion of the wrist of the patient.

In the case of venous restriction, it is preferred that the cuff create less than diastolic pressure so that arteries can pump blood in, but blood does not flow out under the cuff until pressure in limb 44 equals the cuff pressure. Under arterial occlusion, arterial blood is blocked from entering limb 44 and blood drains out of limb 44 through the veins to create a lower blood volume. It has been found that the phase change detected during venous restriction may be different from that detected during arterial occlusion.

It is believed to be easier to implement venous restriction with a blood pressure cuff than it is to perform arterial occlusion. To obtain restriction through occlusion, the ulna and radial arteries should be occluded, which may be difficult. Also, about 10% of the population has a medial artery which should also be occluded. However, it is believed that arterial occlusion drains the large vessels without affecting the capillaries to a great extent while venous restriction has a greater tendency to open up new capillary bends and/or modify the geometry of the vascular space.

Figure 9:
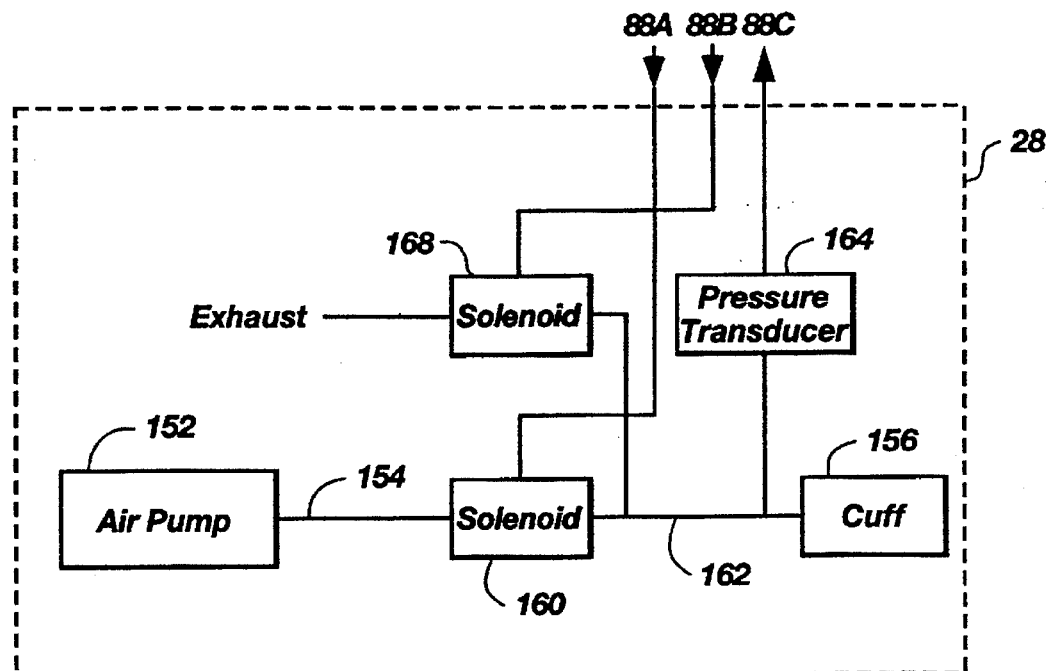
FIG. 9 comprises a more detailed block diagram schematic of the air pump, solenoids, and pressure cuff of FIG. 4.

Referring to FIG. 9, air pump, solenoid(s), and pressure cuff 28 may work as follows. An air pump 152 provides increased air pressure to a tube 154. When it is time for a pressure cuff 156 to increase in pressure, microprocessor 94 activates a solenoid 160 which allows the increased pressure in tube 154 to flow to tube 162. Microprocessor 94 is informed of the pressure in tube 162 through pressure transducer 164. When it is time to decrease the pressure in cuff 156, microprocessor 94 activates solenoid 168 through which tube 162 is connected to an exhaust. Air pump 152 may be turned on under separate switch or under the control of microprocessor 94.

The volume change should be maximized by adjusting the tilt and height of the patient's arm.

It is believed that limb movement may significantly change the impedance.

9. Additional Information

Figure 10:
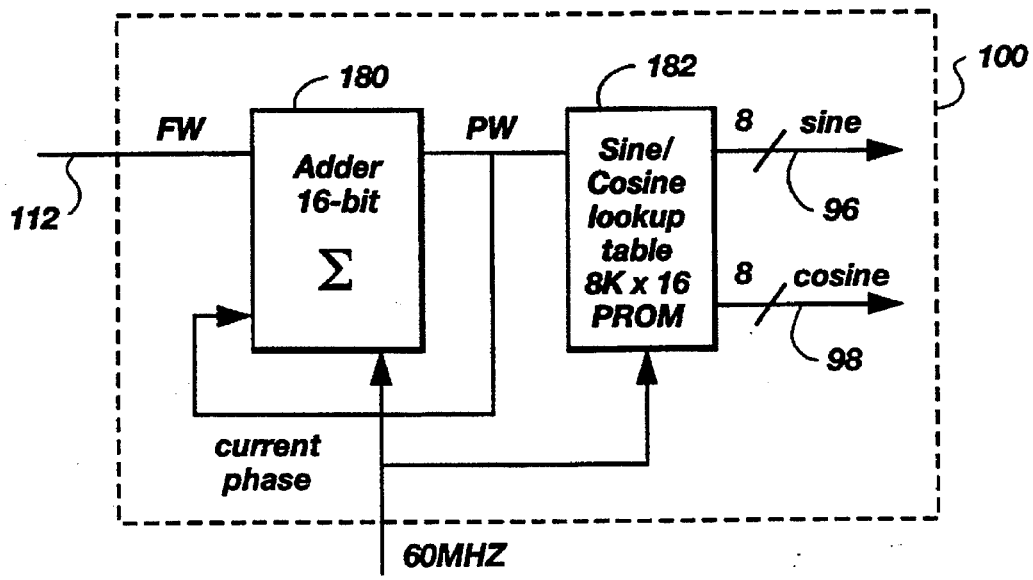
FIG. 10 comprises a more detailed schematic of the frequency generator of FIG. 4.

Frequency generator 100 may be constructed according to a well known practice shown in FIG. 10. Referring to FIG. 10, a 16-bit frequency word FW is received on conductor 112 by an adder 180 that produces a phase word PW in response to the FW. The desired sinusoidal frequency=FW× clock frequency/$2^{16}$. Depending on the maximum desired sinusoidal frequency, the clock frequency may be, for example, 30 or 60 MHz. The phase word PW is received by a sine/cosine look-up table PROM 182 that produces sine and cosine signals. The sine signal may be 127.5×sin (PW× $2\pi$)/2048 and the cosine signal may be 127.5 cos (PW×$2\pi$) /2048. Of course, the preceding is merely an example and various other well known techniques could be used.

Preferably, current is injected into limb 44 between electrodes 48A and 48B, and voltage is measured between electrodes 50A and 50B. Alternatively and less desirably, current could be injected between electrodes 50A and 50B, and voltage measured between electrodes 48A and 48B. In the case of the alternative less desirable arrangement, preferably, both the current injected by electrode 50A and the current received by electrode 50B would be measured to account for any current that may pass to another part of the body. Also, in the case of the alternative less desirable arrangement, it may also be desirable to bring electrodes 50B and 48B closer to electrodes 48A and 50A, and to make the electrodes narrower.

Current could be created through magnetic fields rather than electrodes.

Preferably, the out-of-phase signals on conductors 98 from frequency generator 100 are cosine signals, which are 90 degrees (or 270 degrees) out of phase with the sine signal on conductors 96 (sometimes called a quadrature signal). Alternatively, the out-of-phase signals could have some other relationship than 90 degrees out of phase with respect to sine signals on conductors 96. In that case, it may be necessary and/or desirable to have three or more signals rather than only two signals.

In the illustrated embodiment of FIGS. 4 and 8, the functions of frequency generator 100, low pass filters 116 and 128, and mixers and filters 104 and 106 are performed in hardware (including programmed dedicated hardware with, for example, adders, multipliers, and gate arrays) as opposed to a microprocessor. Alternatively, some or all of the functions may be performed in PC 42, in another microprocessor system, or otherwise in software.

Of course, PC 42 does not have to be a "personal computer" but may be any of various other computers, such as a Macintosh, Sun Microsystems, etc.

Four mixers and filters may be used, rather than the two, eliminating the need for RF switch 80.

As used herein, a "conductor" may actual comprise multiple wires, such as in the case of a parallel digital transmission. In other words, digital data may be transmitted in parallel or in series. There may also be a ground wire. Conductors 38 and 40 each may be a 50 ohm coaxial cable.

As used in the claims, the terms "connect," "connectable," or "connected to" are not necessarily limited to a direct connection.

B. Two-Frequency Embodiments

Although the multi-frequency embodiment described above is generally preferred, a description of the following two-frequency technique for determining the hematocrit is also presented.

1. Background

Referring again to FIG. 1, which depicts an approximation of the behavior of whole blood when subjected to an alternating electrical current, resistance 10 in circuit path 12 represents the response of the extracellular or plasma component, while the parallel circuit path 14, representative of the erythrocyte or red blood corpuscle component, includes both a capacitance 16 as well as a resistance 18. At low frequencies (such as 50 kHz), whole blood impedance is attributable primarily to the extracellular blood component circuit path 12, while at higher frequencies (for example, 1 MHz), the capacitive nature of the cell membrane of the red blood corpuscles results in a more significant impedance contribution from circuit path 14, reducing the magnitude of the whole blood impedance. Thus, in simplified terms, the ratio of a low-frequency impedance to a high-frequency impedance is representative of the relative volume percent of red blood corpuscles, or hematocrit. There is no precise frequency or narrow band at which the red cell capacitance phenomenon becomes significant, but rather a transition zone of frequencies over which the capacitive component increases in a relatively rapid manner. As will be explained in more detail hereafter, the impedance magnitude differential due to the frequency response characteristics of blood below and above the aforementioned transition zone enables the practitioner employing the present invention to utilize electrical stimulation of the patient to determine hematocrit in a noninvasive manner. However, in order to make use of frequency-based impedance differentials in whole blood to determine hematocrit, it is necessary to remove the dominant body tissue impedance component of the body portion through which impedance is measured.

Figure 15:
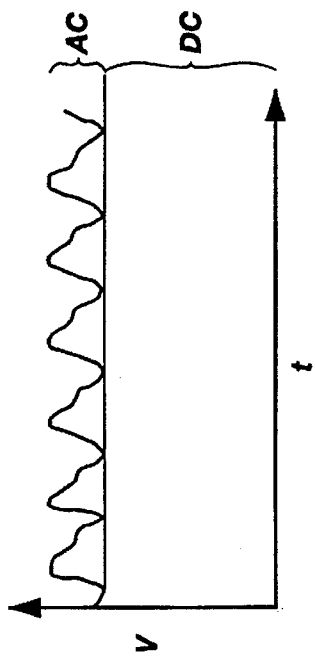
FIG. 15 comprises a graphic, not-to-scale depiction of an analog voltage signal representative of those measured in practicing the present invention showing the relatively small pulsatile component of the signal above the signal baseline.

FIG. 15 of the drawings comprises a representative sector of a demodulated voltage signal envelope over a period of time as measured by sensors attached to an electrically-stimulated extremity of a patient according to the present invention, the measured voltage being directly proportional to and therefore representative of the total impedance of the whole blood plus the surrounding tissue. As shown, the signal envelope includes a dominant DC or baseline component and a small AC or pulsatile component. The DC component is generated by the patient's tissue, non-pulsatile arterial blood, and venous and capillary blood of the stimulated body portion. The AC component is attributable only to the pulsatile blood, and is therefore truly representative of whole blood impedance for a given frequency. AC components at different frequencies will have substantially identical voltage envelope shapes, differing only in magnitude due to the aforementioned frequency-dependent nature of the whole blood impedance response. By isolating and utilizing only the AC, or pulsatile, component of the signal, the impedance effects of the patient's extravascular tissue are eliminated and a hematocrit determination may be made using the ratio of a low-frequency pulsatile impedance to a high-frequency pulsatile impedance.

2. Two-frequency System and Method

Figure 11:
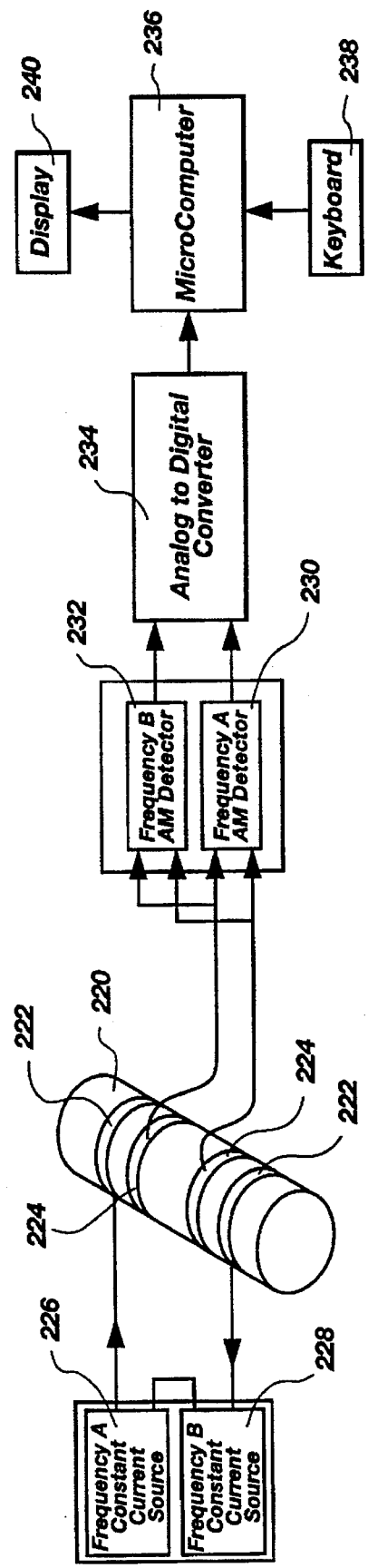
FIG. 11 comprises a combined diagram and schematic of a two-frequency embodiment of the present invention, with electrodes applied to a patient extremity.

FIG. 11, which is illustrative of a two-frequency embodiment of the invention, shows a patient body portion 220 containing an artery (which may also be referred to as a pulsatile vascular compartment) on the exterior of which have been placed outer stimulation electrodes 222 and inner sensor electrodes 224, all of which are preferably ring electrodes so as to envelop the body portion 220. The four-electrode method is a standard engineering technique which helps to eliminate errors attributable to contact resistance and, except insofar as it is employed in the present invention, does not constitute a part thereof.

Power or stimulation electrodes 222 are driven with a constant current composite carrier waveform consisting of two frequencies A and B provided by current sources 226 and 228. It is preferred that the applied constant current be of a peak-to-peak magnitude of 2 mA or less. Frequencies A and B should differ sufficiently to provide a significantly different blood impedance response to each frequency due to the capacitive component of the patient's blood, and thus an impedance differential useful in practicing the present invention. It has been found that a low frequency A of 50 kHz and a high frequency B of 1 MHz provide a usable differential response, in that they are, respectively, sufficiently far below and above the frequency transition zone wherein the capacitive component of the response becomes significant. It should be noted at this point that use of frequencies much below 50 kHz is inadvisable for reasons of patient safety, in that lower frequencies may induce heart arrhythmia.

Each frequency excites the tissue of body portion 220 with a constant current, and the resulting voltage signal at each frequency is measured from inner sensor electrodes 224. Since the current excitation is constant, the envelope of the measured voltage at each frequency is directly proportional to the tissue impedance at that frequency. AM Detectors 230 and 232, one each for frequency A and frequency B, measure the envelope of the voltage signals, and transmit the resulting signals to A/D Converter 234, which converts the signals to the digital domain for isolation of the pulsatile component of the signal and further processing by a programmed processing unit, preferably general purpose Microcomputer 236, in response to commands from Keyboard 238. Microcomputer 236 repeatedly extracts time-matched converted pulsatile signal component segments at each frequency, normalizes them against the voltage baseline of the respective carrier waveforms and then creates a series of segment ratios of the normalized pulsatile signal components. These ratios are averaged, preferably using a weighted averaging methodology which more heavily weights more significant ratios, being those comprised of pulsatile component segments exhibiting the greatest change in voltage magnitude over time. The weighted average of the ratios is representative of the hematocrit, the latter being extracted from an internal look-up table of corresponding ratio and hematocrit values by Microcomputer 236, and displayed to the practitioner via Display 240, which may comprise a graphic screen display, a numerical display, or both.

Figure 12:
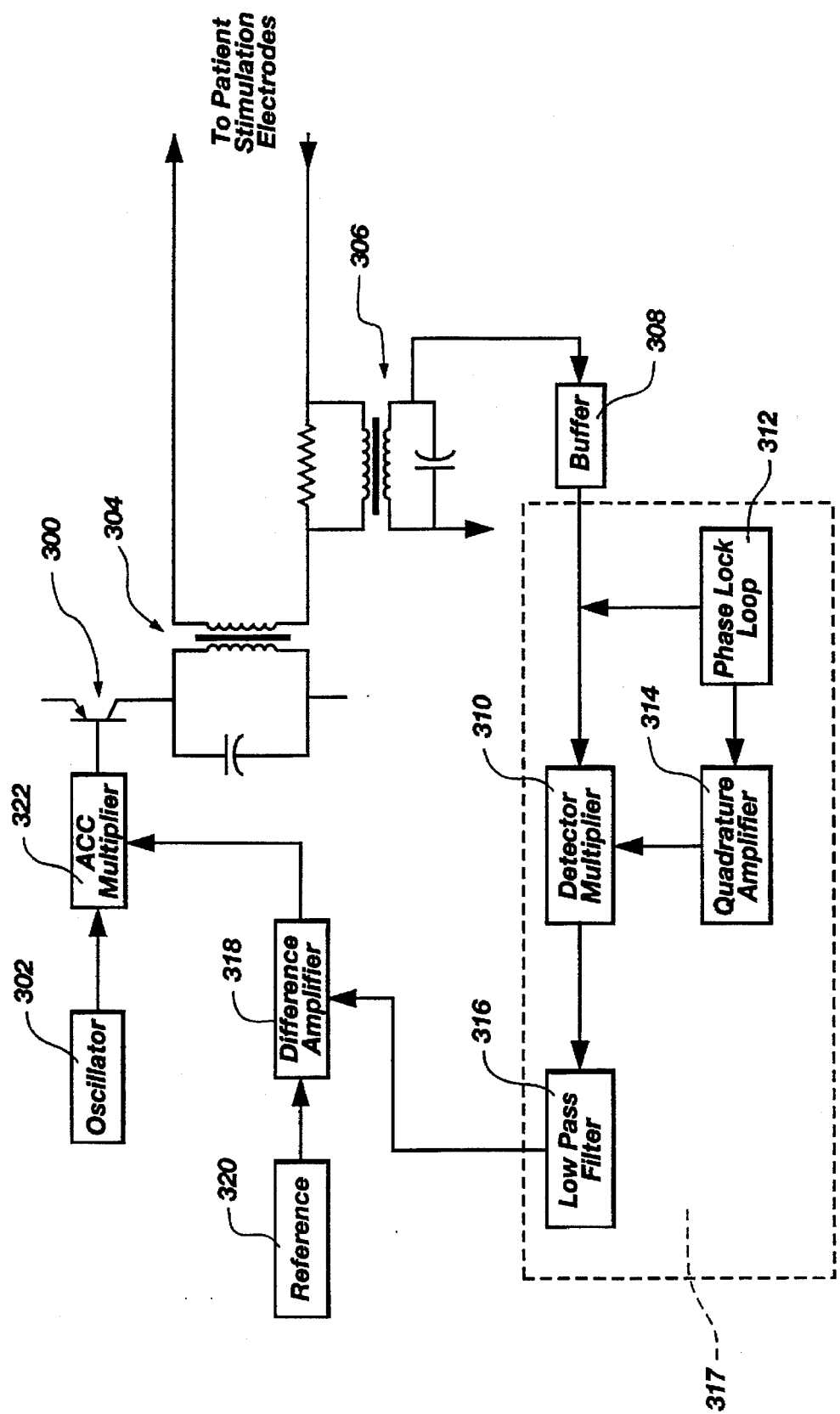
FIG. 12 comprises a schematic of an embodiment of a constant current source as employed in the embodiment of FIG. 11.

An embodiment of current sources 226 and 228 of FIG. 11, as depicted in FIG. 12, uses transistor 300 as an approximation of a current source, which is driven by oscillator 302 through automatic gain control (AGC) multiplier 322 at the desired frequency, the resulting output signal driving power transformer 304 which in turn outputs to patient stimulation electrodes 222. Isolation of each current source using transformer coupling via power transformer 304 and pickoff transformer 306 is used for patient safety. It should be noted that, as is well known in the art, transformers 304 and 306 should be wound to maximize their response at the frequencies of interest and minimize sensitivity to artifact. A sensing or regulator signal is picked off from the output coil of transformer 306 and transmitted through buffer 308 to phase lock loop synchronous AM detector 317, which includes detector multiplier 310, phase lock loop 312, quadrature amplifier 314 and low pass filter 316. Phase lock loops are well known in the art, as are AM synchronous detectors incorporating same, and therefore their structure and function will not be further described herein. However, a brief but excellent description of phase lock loops, their operation, versatility and applications, specifically in the fabrication of an AM synchronous detector suitable for use with the present invention, appears in the 1987 *EXAR Databook*, pp. 6–62 through 65 and 11–68 through 71, published by EXAR Corporation, 2222 Qume Drive, San Jose, Calif. 95131. Detector 317 outputs the envelope of the sensed current drive signal to difference amplifier 318 for comparison to the input signal from reference 320, the output signal from difference amplifier 318 controlling AGC multiplier 322, the output of which is impressed with the desired frequency (A or B) by oscillator 302. Thus a servo-control loop to maintain a substantially constant output from the current source is established. Current sources 226 and 228 are substantially identical except for the frequencies dictated by oscillator 302.

Figure 13:
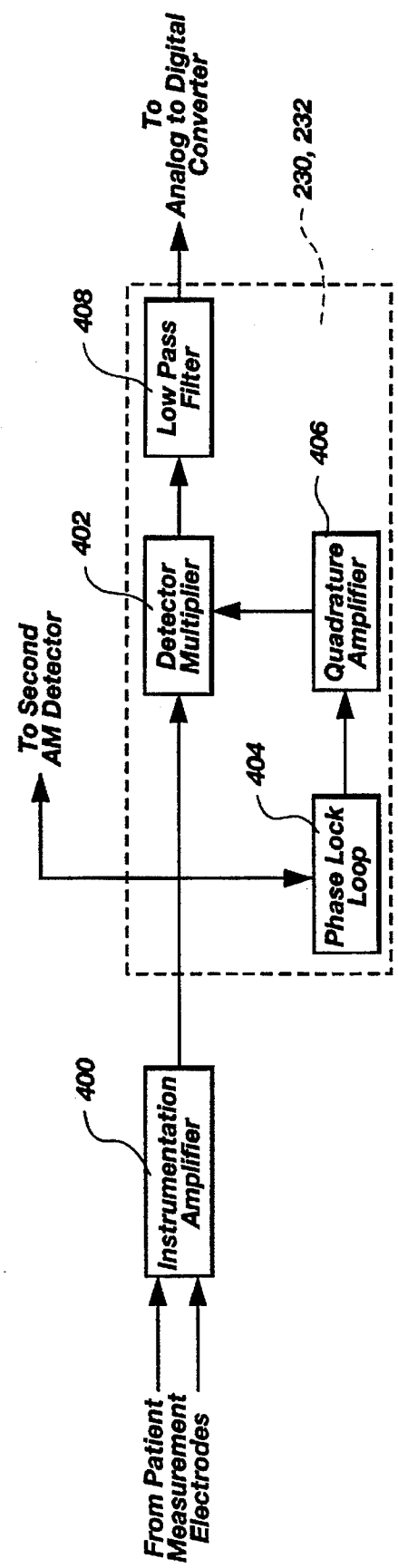
FIG. 13 comprises a schematic of an embodiment of an AM detector as employed in the embodiment of FIG. 11.

The AM Detectors 230 and 232 used in the embodiment of FIG. 11 of the present invention, as depicted in FIG. 13, are AM synchronous detectors built around a phase lock loop. The measured voltage signal from the sensor or patient measurement electrodes 224, which is quite minute, is amplified by instrumentation amplifier 400 and sent to detector multiplier 402 and phase lock loop 404 of each AM Detector 230 and 232, the output of the phase lock loops being filtered by low pass filters 408. The outputs of Detectors 230 and 232 are thus the envelopes of the measured voltage waveforms at low and high frequencies, respectively, and inherently representative of impedance at those frequencies. As noted previously, phase lock loops and synchronous AM detectors, their structure and function are well known in the art, and the reader is again referred to the above-referenced pages of the 1987 *EXAR Databook* for a more detailed description thereof.

Figure 14:
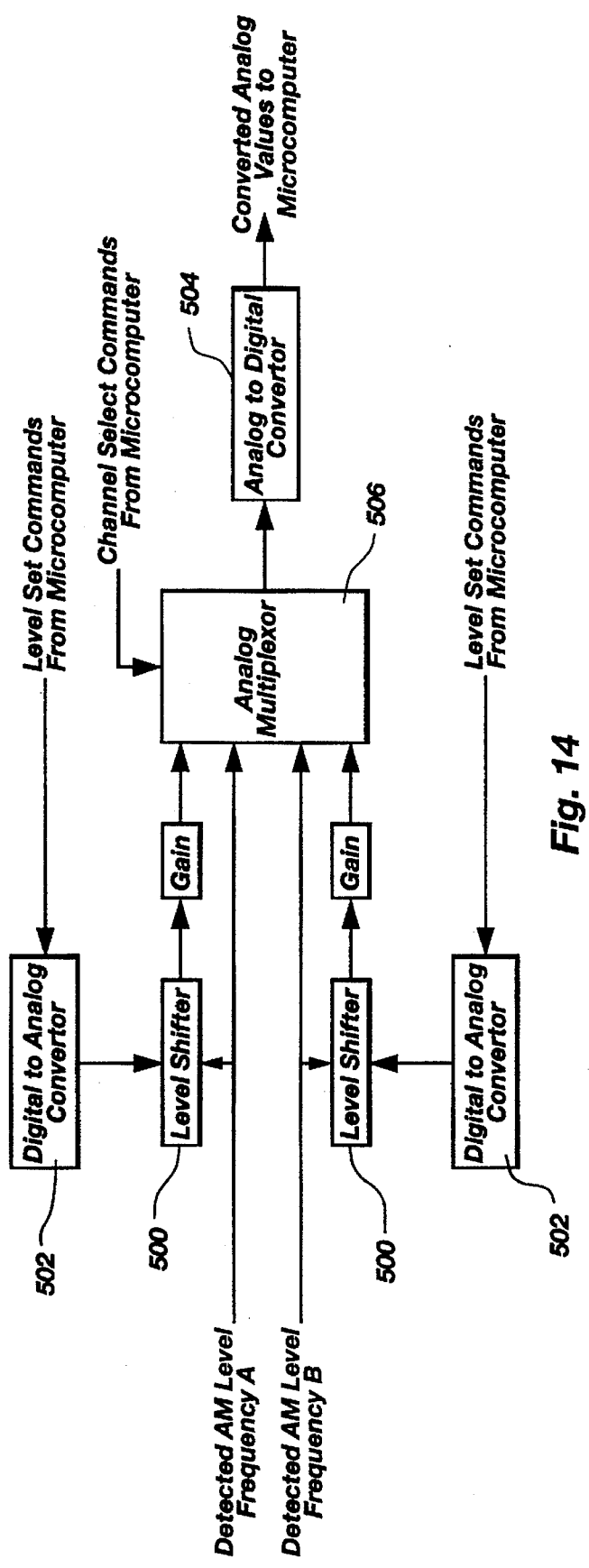
FIG. 14 comprises a schematic of an embodiment of an A/D converter as employed in the embodiment of FIG. 11.

The demodulated voltage signal envelopes from AM Detectors 230 and 232 are received by A/D Converter 234, depicted in its preferred embodiment in FIG. 14, A/D Converter 234 including a pair of level shifters 500, each driven by level set commands from Microcomputer 236 via digital-to-analog (D/A) convertors 502 to extend the range of high resolution analog-to-digital (A/D) converter unit 504 to accommodate the fact that the variable (pulsatile) component of the impedance being measured typically constitutes only about one percent (1%) of the total measured impedance. Analog multiplexor 506 selects the appropriate signals from either AM Detector 230 or 232 responsive to channel select commands from Microcomputer 236, and feeds the selected signal to analog-to-digital converter unit 504 for conversion to the digital domain.

One preferred means of obtaining the pulsatile waveform component of interest in the practice of the present invention is to utilize a high resolution A/D converter unit 504, that is to say, one which has a 20–22 bit resolution capability, and digitize the entire waveform, including both the small AC (pulsatile) and much larger DC (baseline) components. This provides a sufficiently large dynamic range so that the pulsatile, or AC component, of the waveform at each frequency can be isolated to provide meaningful data. However, this approach requires a relatively expensive A/D converter unit, and an alternative approach is to set a voltage clamp level at the magnitude of the DC component, subtract this from the waveform and magnify the remaining signal. The voltage clamp approach is less expensive as it requires fewer bits of resolution capability in the A/D converter unit.

Segments of the converted analog values from Detectors 230 and 232 are then repeatedly extracted over identical time periods by Microcomputer 236, correlated to further reduce noise effects, and then normalized by dividing by the voltage baseline of their respective carrier waveforms before a series of ratios of the time-matched digitized pulsatile component signal segments at frequencies A and B are calculated. The ratios are averaged in a preferred embodiment using weighted averaging techniques well known in the art, relative weighting being based upon the change in voltage magnitude versus time for the time period over which the digitized signals are extracted. Stated another way, the greater the $\Delta V$ per $\Delta t$ for a pair of time-matched component segments, the more significant the resulting ratio and the more heavily the ratio is weighted in the averaging process. The weighted ratio average, which is representative of hematocrit, is correlated to a hematocrit value by Microcomputer 236 via a look-up table of corresponding ratio and hematocrit values constructed a priori from clinical studies and depicted numerically and/or graphically to the practitioner on Display 240. Of course, the foregoing process from measurement of voltage across the patient body portion 220 to ultimate output of patient hematocrit on Display 240 is performed repeatedly and substantially continuously, so that variations and trends in hematocrit will be immediately apparent. The use of empirical data for the look-up table is due to the fact that the electrical approximation employed for the whole blood model is first-order, and a rigorous derivation of the response of the model will be inaccurate. Moreover, any such derivations will yield calibration results which vary with the two frequencies chosen, as well as the gain factors of the various stages of the apparatus.

As will be evident to the skilled practitioner of the art, all components of the apparatus utilized to practice the present invention should be selected for low noise output, due to the extremely low signal magnitude of the signal of interest.

3. Analysis and Comparisons a. The Impedance of Blood

The model for the first-order electrical representation of blood, as shown in FIG. 1, has been established by empirical testing to be correct. It is interesting to note that confirmation of the model has appeared in the biomedical engineering literature. de Vries, P. M. J. M., et al. "Implications of the dielectrical behavior of human blood for continuous on-line measurement of hematocrit", *Med. Biol. Eng. & Comput.* 31, 445–448 (1993).

However, the frequency range of greatest interest, previously believed to lie between 50 kHz and 1 MHz, has been proven to be somewhat different and expanded at the high frequency end. In fact, the preferred frequency range has subsequently been established to lie substantially between 100 kHz and 10 to 20 MHz.

The electrical performance characteristics of blood according to the FIG. 1 model over this latter frequency range (100 kHz and 10 to 20 MHz) have been confirmed by the inventor on numerous occasions with a specially prepared test cell. The test cell was fabricated by taking a cylindrical glass tube 1 cm in diameter. One end was sealed with an insulator containing an embedded electrode. The blood sample was then introduced into the test cell, together with a very small quantity of heparin, to prevent the sample from coagulating in the test cell. A removable stopper of an insulating material was then inserted in the open end of the test cell; the stopper also had an embedded electrode that descended into the blood when the stopper was properly positioned. The impedance characteristic of the blood was then measured in a straight-forward manner (in this configuration, the test cell operates as a two-terminal electrical device) by doing a frequency sweep over the range of interest and measuring the response.

Since stagnant blood has a sedimentation effect, in which the suspended red blood cells will slowly settle due to gravity, it may be important to stir the contents of the test cell if protracted testing is done to ensure reproducibility.

b. The Electrical Model for Noninvasive Hematocrit Determination

Figure 16:
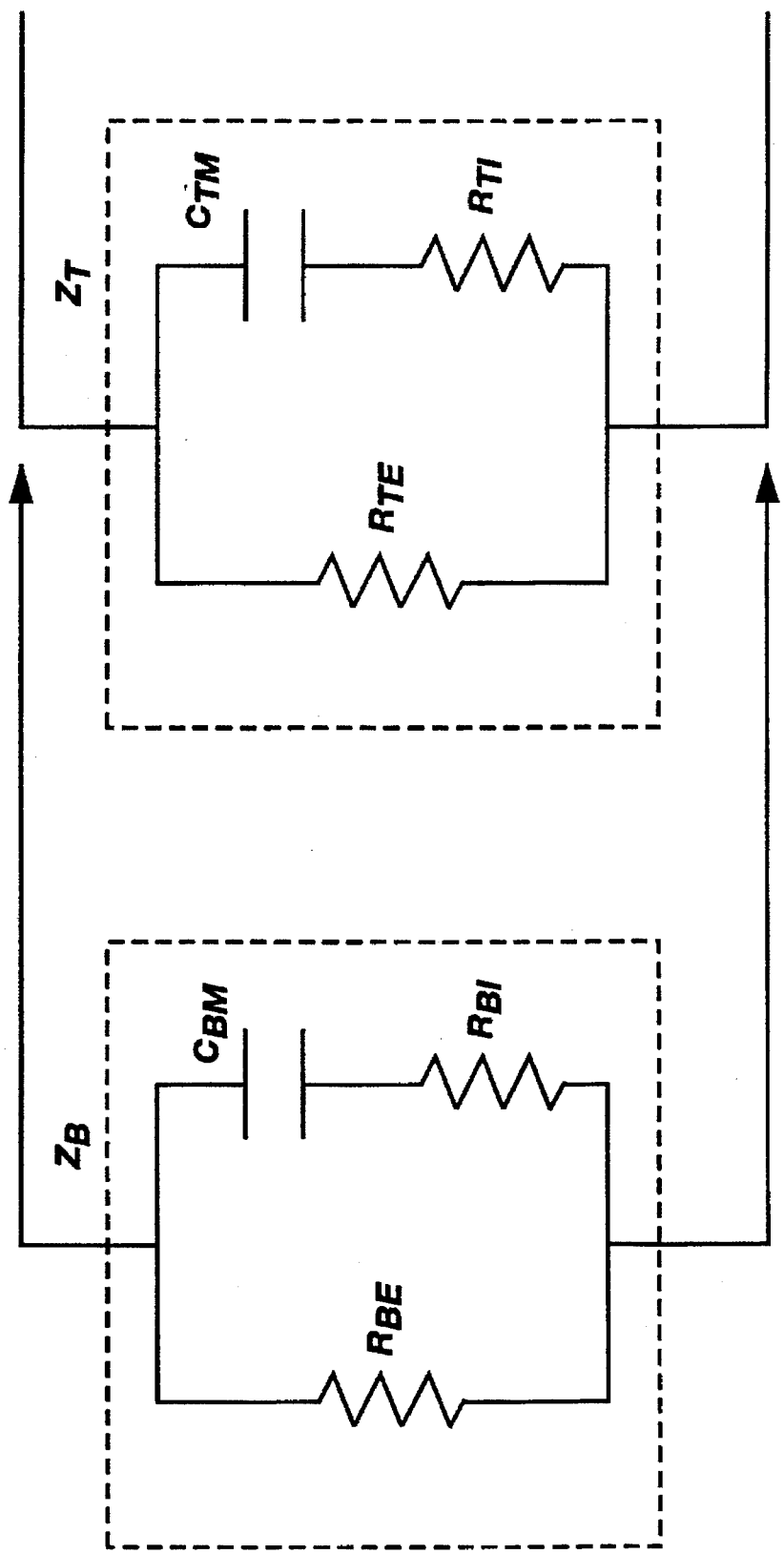
FIG. 16 comprises a circuit schematic for a first-order electrical approximation of the impedance of whole blood in a pulsatile vascular compartment in combination with that of the surrounding tissue in which the compartment is located.

By way of providing those of ordinary skill in the art with a more complete and comprehensive understanding of the invention, it should be reaffirmed that the underlying electrical model is a parallel one. In fact, although the analogy employed in the BACKGROUND section of this application to pulse oximetry might be appropriate for motivation with what is now termed the "small signal" or plethysmographic approach, the analogy would be somewhat inappropriate if carried to an extreme. Specifically, a directly equivalent electrical derivation to the optical problem of pulse oximetry would result in a series electrical model. However, the appropriate electrical model for a body portion 220 under test, as shown in FIG. 11, would be the first order approximation of FIG. 1 representative of the blood in the pulsatile vascular compartment, in parallel with a like circuit, the values of which would represent the intra- and extra-cellular spaces and cell membrane capacitances of the bulk background tissue. This model is shown in FIG. 16, where the background tissue impedance, $Z_T$, is bridged in a parallel fashion by the impedance of an additional volume of blood, $Z_B$. One naturally occurring way in which an additional volume of blood is added to a limb segment is during the cardiac cycle, where the pumping action of the heart causes incremental volumes of blood to be periodically added and removed. As shown in FIG. 16, $Z_B$=Blood Impedance $R_{BE}$=Extracellular Resistance of Blood $R_{BI}$=Intracellular Resistance of Blood $C_{BM}$=Cell Membrane Capacitance $Z_T$=Tissue Impedance $R_{TE}$=Extracellular Resistance of Tissue $R_{TI}$=Intracellular Resistance of Tissue $C_{TM}$=Cell Membrane Capacitance of Tissue The solution of this model is straightforward, and can be done by any electrical engineer of ordinary skill in the art. Successful solution techniques find $Z_B$ by removing the effect of $Z_T$ from the measured gross impedance, using knowledge of the parallel nature of the model. Once $Z_B$ is determined, hematocrit is found to be some function of the ratio $R_{BI}/(R_{BI}+R_{BE})$. The precise characterization of this function cannot be known; however, it is empirically determined during instrument design by making a large number of calibration-type measurements and embedding the results in a look-up table as previously referenced. The look-up table is then employed in the apparatus of the invention as used with a patient in a real-life environment.

Using the underlying concept of measurement at sufficiently low frequencies that the capacitances are essentially open circuits (<100 kHz), and at sufficiently high frequencies that the capacitances are essentially short or closed circuits (>20 MHz), results in simplified equations for solution of the problem.

c. The Two-Frequency Technique

The original inventive concept, as set forth above, addresses the problem (hematocrit determination) from the point of view of impedance magnitude. Since the equivalent electrical circuits used to model the pertinent physiology contain reactive components (capacitors), the impedance across the frequency spectrum is complex; i.e., magnitude and phase are both pertinent (or, equivalently, real and imaginary parts). However, as noted immediately above, by using measurement frequencies that are sufficiently low and sufficiently high, the capacitive components are either respectively open or closed. Thus, the phase at the measurement frequencies would be expected to be at or near zero.

Practically speaking, it is difficult to fabricate electrical devices that perform well at 20 MHz, in order to solve the noninvasive hematocrit determination problem. It is possible, however, to use a two frequency technique where the higher of the two frequencies is lower than 20 MHz if additional assumptions are made. For example, the reverse S-shaped curve plot of blood impedance, Z, which is level at 100 kHz and then slopes downwardly above 100 kHZ until it is again level at 20 MHz, begins to level out at about 10 MHz. Therefore, one may achieve reasonable accuracy by employing a look-up table with high frequency empirical values corresponding to hematocrit as determined at 10 MHz rather than 20 MHz. Alternatively, it is possible to solve the equations represented by the circuits by using more than two frequencies, for example, three or more, if these are chosen so that the measured impedances at these frequencies are sufficiently different from one another. The use of at least one additional frequency would again permit the avoidance of using a 20 MHz high frequency. This technique would involve more mathematics with at least another additional unknown, but potentially is a more refined methodology which might obtain a better approximation of hematocrit at certain levels via curve-fitting than the two-frequency approach.

The approach of the system and method of FIGS. 3–10, however, does not ignore phase. It has been determined that phase angle (phase shift) of a detected waveform relative to the input signal is related to the amount of cell membrane present, and thus to hematocrit. Further, if blood is directly measured in a test cell, as previously described, but both magnitude and phase are recovered, the inventor has found that the phase reaches a maximum response in the vicinity of 1.6 MHz (also confirmed by de Vries, et al, previously cited). This is the frequency region approximately corresponding to the point of inflection of the reverse S-shaped impedance/frequency curve. Thus, if appropriate hardware is fabricated, the noninvasive hematocrit determination problem can be solved with a two frequency measurement employing the phase of the detected signals in combination with impedance magnitude, wherein the high frequency is significantly lower than 20 MHz.

d. The Modified Small Signal Approach

As discussed earlier with respect to the two-frequency embodiment of the invention, when a limb containing a pulsatile vascular space is measured electrically, the pulsatile component (known as the plethysmographic signal) is a very small percentage of the baseline DC signal. Typically, this plethysmographic signal is 0.05–0.1% of the magnitude of the baseline. This in itself requires very rigorously designed instrumentation, as heretofore noted, because of the necessary dynamic range.

However, an additional problem has been discovered with the small signal approach as described with respect to the two-frequency embodiment of the invention. This problem is due to the nature of intracorporeal blood-flow, which the inventor has determined to be non-homogeneous. By this, it is meant that the gross components of blood, namely plasma and the suspended cellular particles, do not flow in lock-step with one another; rather, in response to irregular paths, turbulence, etc., the concentration of red cells in plasma may exhibit regions of higher concentration followed by regions of lower concentration. Thus, over the course of a cardiac cycle, there will be small changes in the "instantaneous hematocrit" at any given point in a vascular space. Thus, if one could station a miniature "perfect observer" at a given point in an artery, this observer might detect instantaneous hematocrits varying from 39 to 41 in a person whose classically measured hematocrit was 40.

While seemingly small in absolute terms, such variations in instantaneous hematocrit tend to have a rather large effect on the derived hematocrit when the noninvasive technique of the invention is used. This phenomenon results from the underlying assumption that the plethysmographic variations that are observed are due strictly to variations in the observed volume of whole blood, and are representative of whole blood. In fact, the measured variations are a combination of true blood volume change as well as changes in the local density of red cells in plasma. It is conceivable that the relative percentage of the density variation is actually larger than the plethysmographic percentage of the baseline. This situation may lead to markedly incorrect results, even if an ideal apparatus were to be built.

A solution to the aforementioned problem with using the small signal approach created by variations in instantaneous hematocrit is to restore correctness to the underlying assumption of homogeneity of blood flow. This modified small signal approach is effected by applying a mechanical "assist" to the limb under measurement. To understand the basis for this "assist," consider what happens when a blood pressure cuff is applied to a limb and taken through an inflation-deflation cycle. When the cuff is initially taken up to a pressure that exceeds systolic blood pressure by a fair amount, the pressure results in the complete obliteration of the arterial space; consequently, no blood will flow past the obstruction effected by the cuff at any point in the cardiac cycle and the plethysmographic signal is completely suppressed. As the cuff bleed valve is opened and the cuff is deflated slowly, the column of blood at the proximal end of the cuff is able to make brief incursions into the region of the limb under the cuff during the high pressure parts of the cardiac cycle. Just as the cuff deflates to systolic pressure, a small quantity of blood is able to completely traverse the occluded zone for just a brief instant. As the cuff pressure continues to decrease, a larger fraction of blood is able to transit through the occlusion zone, although there is still complete occlusion of the artery for the portion of the cardiac cycle that has a pressure below the occluding cuff pressure. Finally, as the cuff deflates to diastolic blood pressure, the blood is able to travel past the occlusion zone for the entire cardiac cycle.

Now, consider again the situation where the cuff pressure is just at the systolic value. The tiny fraction of blood that is able to completely traverse the occlusion zone is nearly pure plasma, because plasma is less viscous than whole blood and the resistance of the nearly totally occluded artery is very high. As the cuff pressure continues to decrease, the resistance presented to the blood also decreases, and more cellular components are able to flow. The desirable effect being sought is one where the artery remains occluded for at least a small portion of the cardiac cycle and where the blood traversing the occlusion zone is representative of whole blood, at least over time.

Thus, by causing the artery to be occluded by a blood pressure cuff during a portion of the cardiac cycle, it is guaranteed that the plethysmographic signal is representative of the total volume of blood in the artery, rather than the small portion of additional volume due to cardiac ejection. Additionally, if the blood traversing the occlusion zone is representative of whole blood over time, then the plethysmographic waveform can be integrated to solve the problem.

It has been found that the proper conditions to effect the foregoing desired result occur when the cuff pressure is in the region of mean arterial pressure. This pressure zone is non-critical and corresponds to the pressure region where the amplitude of the plethysmographic component of the signal becomes a maximum.

To practice the invention according to this methodology, the cuff is applied to the body portion (limb) in question proximate the stimulation and sensor electrodes. It is feasible to place the cuff either proximally, distally or over the electrodes, there at present being no identified preferred location for the cuff relative to the electrodes. Pressure in the cuff and inflation and deflation thereof may be controlled via a pump, bleed valve and sensor (pressure transducer) as known in the art, which devices are preferably under control of the microcomputer of the hematocrit determination apparatus.

It should also be observed that the modified small signal approach should be employed with simultaneous stimulation of the body portion in question at the two selected frequencies, due to the importance of fairly precise synchronization of sampling with the timing of the cuff inflation/deflation cycle.

e. The Large Signal Approach

The multi-frequency approach described in connection with FIGS. 3–10 is referred to as a large signal approach. By contrast, the two-frequency approach is referred to as a small signal approach. An underlying impedance effect has been discovered and verified that allows the determination of hematocrit using electrical measurements. The concept is extended to the noninvasive realm by observing blood plus background tissue and focusing in on the component that is due to blood; i.e., subtracting out the portion of the effect that is due to the background tissue. Naturally occurring variations in blood volume due to the actions inherent in the cardiac cycle are used by measuring the plethysmographic signals. In the previously-discussed small signal approach, a blood pressure cuff is employed to avoid the deleterious effects of the non-homogeneous nature of blood flow.

A large shift in blood is effected by the system and method described in connection with FIGS. 3–10. The nature of the method is such that blood flow artifact is eliminated. The same concept of subtracting out the background tissue impedance is employed, using the equations that result from solving the parallel model.

The procedure requires that an initial measurement of the background be taken with the limb under examination at rest, a blood pressure cuff having been previously applied. The cuff is then inflated to a point that is just below diastolic blood pressure. This pressure level allows blood flow during the complete cardiac cycle through the arteries; however, the cuff pressure is sufficient to provide venous occlusion. For purposes of convenience, a vein may also be referred to as a non-pulsatile vascular compartment. Thus, a situation has been created where whole blood is being added to the limb while outflow of blood is prevented. This serves to temporarily sequester an additional volume of whole blood in the vascular space of the limb. If, now, an additional measurement is taken, it becomes a simple matter using the aforementioned background measurement in combination with the additional measurement to apply the equations that solve the parallel model (FIG. 16) to derive the hematocrit. It has been determined that the differential signal magnitude that results as a consequence of this maneuver is on the order of 2–5%, which is a significant improvement over the magnitude of the plethysmographic signal in comparison to the baseline. It should also be noted that the large signal approach is a static technique in which the sequestered increment of blood is not flowing during the period of measurement. As a result, the artifact due to non-homogeneous blood flow is eliminated. Further, because the large signal approach is a static technique, stimulation of the patient body portion at different frequencies may be effected sequentially rather than simultaneously, via sweeping or rapidly sampling at the desired frequencies.

The operation of the blood pressure cuff to effectuate the large signal approach is preferably controlled, as with the small signal approach, by the microcomputer of the hematocrit determination apparatus.

C. Measurement of Blood Pressure

Since the measurement setup for both the modified small signal and the large signal approach involves the application of a blood pressure cuff, as well as the electrodes necessary for impedance measurement, the apparatus may also be used to provide for the measurement of blood pressure using a different technique than that which is commonly employed in present day noninvasive automatic blood pressure monitors.

Current technology for automatic blood pressure monitoring generally employs the oscillometric approach. This involves analysis of the pressure variation in the blood pressure cuff itself that is due to pulsation in the arteries that underlay the cuff. Such an approach has been recognized to result in reasonably accurate values for systolic and mean blood pressures, but usually inaccurate values for diastolic blood pressure. However, the oscillometric technique has found widespread acceptance due to the simplicity, from the user's point-of-view, of employing the cuff as both the medium of pressure application as well as the sensing device. This results in a favorably perceived trade-off between inaccuracy of measurement of diastolic pressure versus ease-of-use.

Although the blood pressure determination technique of the invention involves the connection of additional interfaces to the patient, this is already being done to obtain the hematocrit noninvasively. Therefore, it is attractive to use the apparatus of the invention to also obtain a blood pressure reading that is, in fact, more accurate than that afforded by the oscillometric technique.

The measurement points of interest using a blood pressure cuff and impedance determination electrodes and circuitry are found as follows: the cuff is inflated initially to suppress the plethysmographic signal; as the cuff is deflated, systolic pressure is the point at which the plethysmographic waveform reappears; as cuff deflation continues, mean arterial pressure is the point of maximum intensity of the plethysmographic signal; as cuff deflation continues still further, diastolic pressure is that at which the morphology of the plethysmographic waveform ceases to undergo further change with continued cuff deflation.

D. Conclusion

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed.

What is claimed is:

1. A system for noninvasive determination of hematocrit of blood in a body portion of a patient, the system comprising:

signal generation circuitry to produce alternating and quadrature signals at various frequencies;

processing, sensing, and application circuitry to provide current signals through the body portion in response to the alternating signals, and to sense the current signals being applied and produce current indicating signals in response thereto, and to sense voltage signals over a section of the body portion and produce voltage indicating signals in response thereto;

processing and demodulation circuitry to receive and mix the current indicating signals and the alternating and quadrature signals to produce inphase and quadrature current representing signals, and to receive the voltage indicating signals and mix the voltage indicating signals and the alternating and quadrature signals to produce inphase and quadrature voltage representing signals; and evaluation circuitry to receive and process the inphase and quadrature current representing signals and inphase and quadrature voltage representing signals to determine the hematocrit.

2. The system of claim 1 in which the evaluation circuitry includes a neural network in which parameters of the processed inphase and quadrature current representing signals and inphase and quadrature voltage representing signals are included in a comparison with pre-gathered data to determine the hematocrit.

3. The system of claim 2 in which parameters regarding the patient are also included in the comparison.

4. The system of claim 2 in which the pre-gathered data includes parameters regarding processed inphase and quadrature current representing signals and inphase and quadrature voltage representing signals of various persons other than the patient.

5. The system of claim 1 in which the evaluation circuitry has access to and considers a group of hematocrit data representative of numerous persons.

6. The system of claim 1 further comprising a blood flow restriction device for restricting flow of blood in the body portion, thereby allowing blood volume in the body portion to change between at least a first and a second volume; and in which the processing, sensing, and application circuitry produces current indicating signals and voltage indicating signals for at least the first and second volumes.

7. The system of claim 6 in which the blood flow restriction device includes a pressure cuff.

8. The system of claim 1 in which the body portion includes a portion of a finger of the patient.

9. The system of claim 1 in which the various frequencies range from 10 kHz to 10 MHz.

10. The system of claim 1 in which the processing and demodulation circuitry is included in a microprocessor system.

11. The system of claim 1 in which the signal generation circuitry is included in a microprocessor system.

12. The system of claim 1 in which the processing and demodulation circuitry and the signal generation circuitry are included in a microprocessor system.

13. The system of claim 1 in which the processing, sensing, and application circuitry includes a switch through which the voltage indicating signals and current indicating signals alternatively pass.

14. The system of claim 1 in which the processing and demodulation circuitry includes low pass filters with outputs and the inphase and quadrature current representing signals, and inphase and quadrature voltage representing signals are provided at the outputs of the low pass filters.

15. A system for noninvasive determination of hematocrit of blood of a patient, the system comprising:

signal generation circuitry to produce alternating signals at various frequencies and out-of-phase signals with respect to the alternating signals;

processing, sensing, and application circuitry to provide current signals through the blood in response to the alternating signals, and that senses the current signals being applied and produces current indicating signals in response thereto, and that senses voltage signals over a section of the blood and produces voltage indicating signals in response thereto;

processing and demodulation circuitry to receive and mix the current indicating signals and the alternating and out-of-phase signals to produce inphase and out-of-phase current representing signals and to receive the voltage indicating signals and mix the voltage indicating signals and the inphase and out-of-phase voltage representing signals to produce inphase and out-of-phase voltage representing signals; and evaluation circuitry to receive and process the inphase and out-of-phase current representing signals and inphase and out-of-phase voltage representing signals to determine the hematocrit.

16. The system of claim 15 in which the evaluation circuitry includes a neural network in which parameters of the processed inphase and out-of-phase current representing signals and inphase and out-of-phase voltage representing signals are included in a comparison with pre-gathered data to determine the hematocrit.

17. The system of claim 16 in which parameters regarding the patient are also included in the comparison.

18. The system of claim 16 in which the pre-gathered data includes parameters regarding processed inphase and out-of-phase current representing signals and inphase and out-of-phase voltage representing signals of other persons.

19. The system of claim 15 in which the section of blood is in a limb of the patient, and further comprising a blood flow restriction device for restricting flow of blood in a limb, thereby allowing blood volume in a limb to change between at least a first and a second volume; and in which the processing, sensing, and application circuitry produces current indicating signals and voltage indicating signals for at least the first and second volumes.

20. The system of claim 15 in which the processing, sensing, and application circuitry includes two outer electrodes and two inner electrodes applied to the housing portion of the patient, and the current signals are applied through the two outer electrodes and the voltage signals are sensed through the two inner electrodes.

21. The system of claim 15 in which the processing, sensing, and application circuitry includes two outer electrodes and two inner electrodes applied to the body portion of the patient, and the current signals are applied through the two inner electrodes and the voltage signals are sensed through the two outer electrodes.

22. A system for noninvasive determination of hematocrit of blood in a body portion of a patient, the system comprising:

signal generation means for producing alternating and quadrature signals at various frequencies;

processing, sensing, and application means for providing first signals through the body portion in response to the alternating signals, and sensing the first signals being applied and producing first indicating signals in response thereto, and sensing second signals over a section of the body portion and producing second indicating signals in response thereto;

processing and demodulation means for receiving and mixing the first indicating signals and the alternating and quadrature signals to produce inphase and quadrature first representing signals, and receiving the second indicating signals and mixing the second indicating signals and the alternating and quadrature signals to produce inphase and quadrature second representing signals; and evaluation means for receiving and processing the inphase and quadrature first representing signals and inphase and quadrature second representing signals to determine the hematocrit.

23. The system of claim 22 in which the evaluation means includes a neural network in which parameters of the processed inphase and quadrature first representing signals and inphase and quadrature second representing signals are included in a comparison with pre-gathered data to determine the hematocrit.

24. The system of claim 23 in which parameters regarding the patient are also included in the comparison.

25. The system of claim 23 in which the pre-gathered data includes parameters regarding processed inphase and quadrature first representing signals and inphase and quadrature second representing signals of other persons.

26. The system of claim 22, wherein the first signals are current signals and the second signals are voltage signals.

27. A method for noninvasive determination of hematocrit of blood in a body portion of a patient, the method comprising:

injecting alternating current signals having various frequencies into the body portion at different blood volumes, the injected alternating current signals being responsive to generated alternating signals having the various frequencies;

providing current indicating signals representative of the current signals injected into the body portion;

measuring voltage signals across a section of the body portion through which the current signals pass;

providing voltage indicating signals representative of the measured voltage signals;

mixing the current indicating signals with the generated alternating signals and with quadrature signals to produce inphase and quadrature current representative signals;

mixing the voltage indicating signals with the generated alternating signals and with the quadrature signals to produce inphase and quadrature voltage representative signals; and determining the hematocrit by considering parameters of the inphase and quadrature current representative signals and the inphase and quadrature voltage representative signals.

28. The method of claim 27 in which the step of determining the hematocrit includes employing a neural network in which parameters of the processed inphase and quadrature current representing signals and inphase and quadrature voltage representing signals are included in a comparison with pre-gathered data to determine the hematocrit.

29. A system for developing a group of data with which a hematocrit of blood of a particular patient may be determined, the system comprising:

signal generation circuitry that produces alternating and quadrature signals at various frequencies;

processing, sensing, application circuitry that provides current signals through a body portion of numerous patients in response to the alternating signals, and that senses the current signals being applied and produces current indicating signals in response thereto, and that senses voltage signals over a section of the body portion and produces voltage indicating signals in response thereto; and processing and demodulation circuitry that receives and mixes the current indicating signals and the alternating and quadrature signals to produce inphase and quadrature current representing signals, and receives and mixes the voltage indicating signals and the alternating and quadrature signals to produce inphase and quadrature voltage representing signals; and evaluation circuitry that receives and processes the inphase and quadrature current representing signals and inphase and quadrature voltage representing signals and compares parameters of the inphase and quadrature current representing signals and inphase and quadrature voltage representing signals with various pre-gathered data to produce the group of data.

30. An apparatus for noninvasive determination of the relative volume percent of erythrocytes, also termed the hematocrit, of blood having an impedance, comprising:

means for producing a constant current at a first low and at least one second high carrier wave frequencies, said first low frequency being below a frequency zone within which said erythrocytes significantly affect the magnitude of the impedance of said blood, and said at least one second high frequency being within said frequency zone;

means for stimulating a patient body portion including at least one pulsatile vascular compartment containing said blood with said first low and said at least one second high carrier wave frequencies;

means for sensing voltage signals at each of said first low and said at least one second high carrier wave frequencies across said stimulated patient body portion;

means for amplifying said sensed voltage signals;

means for demodulating said amplified, sensed voltage signals to produce at least two complex waveforms respectively proportional to the magnitude of impedance of said blood at said first low and said at least one second high carrier wave frequencies; and means for processing said at least two complex waveforms to determine said hematocrit of said blood.

31. The apparatus of claim 30, wherein said means for producing a constant current at said first low and said at least one second high carrier wave frequencies comprises a signal generator in combination with a constant current amplifier, and said means for processing determines said first low and said at least one second high carrier wave frequencies.

32. The apparatus of claim 31, wherein said signal generator includes a first and a second adder paired respectively with a first and a second sine/cosine look-up table to produce each of said first low and said at least one second high carrier wave frequencies.

33. The apparatus of claim 32, wherein said first and second look-up tables each produce a sine output, and said signal generator further includes a third adder for summing said outputs and an analog-to-digital converter for converting said summed sine outputs to the digital domain for receipt by said constant current amplifier.

34. The apparatus of claim 31, wherein said signal generator generates a voltage waveform for conversion by said constant current amplifier to a constant current source.

35. The apparatus of claim 30, wherein said means for amplifying comprises a voltage detector.

36. The apparatus of claim 35, wherein said voltage detector comprises an instrumentation amplifier with common mode rejection.

37. The apparatus of claim 30, wherein said means for demodulating comprises a signal generator and a signal demodulator.

38. The apparatus of claim 37, wherein said signal generator includes a first and a second adder paired, respectively, with a first and a second sine/cosine look-up table, to produce each of said first low and said at least one second high carrier wave frequencies.

39. The apparatus of claim 38, wherein said signal demodulator includes a paired low-pass filter and an analog-to-digital converter for receiving said amplified voltage signals.

40. The apparatus of claim 39, wherein said signal demodulator further includes a first, second, third and fourth mixer paired, respectively, with a first, second, third and fourth digital low-pass filter, each of said mixer/filter pairs receiving the output of said paired low-pass filter and analog-to-digital converter and one of a first sine output or a first cosine output from said first look-up table or a second sine output or a second cosine output from said second look-up table, said paired mixers and digital low-pass filters outputting said at least two complex waveforms.

41. The apparatus of claim 30, wherein said first low carrier wave frequency lies at about 100 kHz, and said at least one second high carrier wave frequency lies within the range from about 10 MHz to about 20 MHz.

42. The apparatus of claim 30, further comprising means for selectively occluding said at least one pulsatile vascular compartment.

43. The apparatus of claim 42, wherein said selective occlusion comprises partial occlusion.

44. The apparatus of claim 43, wherein said selective occlusion comprises substantially total occlusion.

45. The apparatus of claim 42, wherein said means for selectively occluding comprises an inflatable cuff surrounding said patient body portion.

46. The apparatus of claim 45, wherein said selective occlusion is performed by pressurizing said cuff in the region of the mean pressure of said at least one pulsatile vascular compartment.

47. The apparatus of claim 42, wherein said means for selectively occluding is located on said patient body portion proximate said means for stimulating and said means for sensing.

48. The apparatus of claim 42, wherein said means for selectively occluding is controlled by said means for processing.

49. The apparatus of claim 30, wherein said patient body portion further includes at least one non-pulsatile vascular compartment, and said apparatus further includes means for selectively occluding said at least one non-pulsatile vascular compartment while said at least one pulsatile vascular compartment remains unoccluded.

50. The apparatus of claim 49, wherein said means for selectively occluding comprises an inflatable cuff surrounding said patient body portion.

51. The apparatus of claim 49, wherein said means for selectively occluding is controlled by said means for processing.

52. The apparatus of claim 30, further comprising means for compensating for non-homogeneous flow of said blood through at least one said pulsatile vascular compartment in determining said hematocrit of said blood.

53. The apparatus of claim 30, further comprising means for determining blood pressure of said blood in said at least one pulsatile vascular compartment.

54. The apparatus of claim 53, wherein said means for determining said blood pressure includes means for selectively occluding said at least one pulsatile vascular compartment.

55. The apparatus of claim 54, wherein said means for selectively occluding at least one said pulsatile vascular compartment is controlled by said means for processing to completely occlude said at least one pulsatile vascular compartment, and to subsequently reduce said complete occlusion by a degree sufficient to induce the appearance of a plethysmographic waveform signal at said means for sensing, to further reduce said occlusion by a degree sufficient to maximize the intensity of said plethysmographic waveform signal, and to still further reduce said occlusion until said plethysmographic waveform undergoes no further change.

56. The apparatus of claim 55, wherein said appearance of said plethysmographic waveform is indicative of systolic pressure of said at least one pulsatile vascular compartment, said maximum signal intensity of said plethysmographic signal is indicative of mean pressure of said at least one pulsatile vascular compartment, and said point at which said plethysmographic waveform ceases to change is indicative of diastolic pressure of said at least one pulsatile vascular compartment.

57. The apparatus of claim 56, wherein said means for selectively occluding comprises a cuff disposed about said patient body portion and inflatable to a pressure sufficient to occlude said at least one pulsatile vascular compartment, and said indication of said systolic, mean and diastolic pressure of said at least one pulsatile vascular compartment is correlated to the actual systolic, mean and diastolic pressures of said at least one pulsatile vascular compartment by pressure transducer means associated with said cuff, the output of which is converted by said processing means to said actual pressures.

58. The apparatus of claim 30, wherein said means for producing a constant current comprises means for producing said current at a plurality of said second high carrier wave frequencies.

59. The apparatus of claim 30, wherein said means for processing said at least two complex waveforms employs the magnitudes thereof to determine said hematocrit of said blood.

60. The apparatus of claim 30, wherein said means for processing said at least two complex waveforms employs the magnitudes and phases thereof to determine said hematocrit of said blood.

61. The apparatus of claim 30, wherein said first low carrier wave frequency lies at about 100 kHz, and said at least one second high carrier wave frequency lies between 100 kHz and about 10 MHz.

62. A method for noninvasive determination of the relative volume percent of erythrocytes, also termed the hematocrit, of blood having an impedance, comprising:
   producing a constant current at a first low and at least one second high carrier wave frequencies, said first low frequency being below a frequency zone within which said erythrocytes significantly affect the magnitude of the impedance of said blood, and said at least one second high frequency being within said frequency zone;
   stimulating a patient body portion including at least one pulsatile vascular compartment containing said blood with said first low and said at least one second high carrier wave frequencies;
   sensing voltage signals at each of said first low and said at least one second high carrier wave frequencies across said stimulated patient body portion;
   amplifying said sensed voltage signals;
   demodulating said amplified, sensed voltage signals to produce at least two complex waveforms respectively proportional to the magnitude of impedance of said blood at said first low and said at least one second high carrier wave frequencies; and
   processing said at least two complex waveforms to determine said hematocrit of said blood.

63. The method of claim 62, further comprising producing said constant current at a plurality of said second high carrier wave frequencies.

64. The method of claim 62, wherein processing said at least two complex waveforms employs the magnitudes thereof to determine said hematocrit of said blood.

65. The method of claim 62, wherein processing said at least two complex waveforms employs the magnitudes and phases thereof to determine said hematocrit of said blood.

66. The method of claim 62, wherein said first low carrier wave frequency lies at about 100 kHz, and said at least one second high carrier wave frequency lies within the range from about 10 MHz to about 20 MHz.

67. The method of claim 62, wherein said first low carrier wave frequency lies at about 100 kHz, and said at least one second high carrier wave frequency lies between 100 kHz and about 10 MHz.

68. The method of claim 62, further comprising selectively occluding said at least one pulsatile vascular compartment.

69. The method of claim 68, wherein said selective occlusion comprises partial occlusion.

70. The method of claim 68, wherein said selective occlusion comprises substantially total occlusion.

71. The method of claim 68, wherein said selective occlusion is effected by applying pressure about said at least one pulsatile vascular compartment in the region of the mean pressure of said at least one pulsatile vascular compartment.

72. The method of claim 68, wherein said selective occlusion is effected on said patient body portion proximate locations thereon wherein said stimulating and said sensing are performed.

73. The method of claim 62, wherein said patient body portion further includes at least one non-pulsatile vascular compartment, and said method further includes selectively occluding said at least one non-pulsatile vascular compartment while said at least one pulsatile vascular compartment remains unoccluded.

74. The method of claim 62, further comprising compensating for non-homogeneous flow of said blood through said at least one pulsatile vascular compartment in determining said hematocrit of said blood.

75. The method of claim 62, further comprising determining blood pressure of said blood in said at least one pulsatile vascular compartment.

76. The method of claim 75, wherein said determining said blood pressure includes selectively occluding said at least one pulsatile vascular compartment.

77. The method of claim 76, wherein said at least one selective occlusion of said pulsatile vascular compartment for determination of blood pressure includes completely occluding said at least one pulsatile vascular compartment, subsequently reducing said complete occlusion by a degree sufficient to induce the appearance of a plethysmographic waveform signal, to further reduce said occlusion by a degree sufficient to maximize the intensity of said plethysmographic waveform signal, and to still further reduce said occlusion until said plethysmographic waveform undergoes no further change.

78. The method of claim 77, wherein said appearance of said plethysmographic waveform is indicative of systolic pressure of said at least one pulsatile vascular compartment, said maximum signal intensity of said plethysmographic signal is indicative of mean pressure of said at least one pulsatile vascular compartment, and said point at which said plethysmographic waveform ceases to change is indicative of diastolic pressure of said at least one pulsatile vascular compartment.

79. The method of claim 78, further including selectively occluding using a cuff disposed about said patient body portion and inflatable to a pressure sufficient to occlude said pulsatile vascular compartment, and said indication of said systolic, mean and diastolic pressure of said pulsatile vascular compartment is correlated to the actual systolic, mean and diastolic pressures of said vascular compartment by pressure transducer means associated with said cuff, the output of which is processed to said actual pressures.

80. An apparatus for determining blood pressure in a pulsatile vascular compartment of a patient body portion containing blood, comprising:
   means for producing a constant current at a carrier wave frequency;
   means for stimulating said patient body portion including said pulsatile vascular compartment containing said blood with said constant current;
   means for sensing a voltage signal at said carrier wave frequency across said stimulated patient body portion;
   means for amplifying said sensed voltage signal;
   means for demodulating said amplified, sensed voltage signal to produce a plethysmographic waveform signal;
   means for sensing the existence, magnitude and shape of said plethysmographic waveform signal;
   means for selectively occluding said pulsatile vascular compartment to completely occlude said pulsatile vascular compartment and suppress said plethysmographic waveform signal, to subsequently reduce said complete occlusion by a degree sufficient to induce the appearance of said plethysmographic waveform signal, to further reduce said occlusion by a degree sufficient to maximize the intensity of said plethysmographic waveform signal, and to still further reduce said occlusion until said plethysmographic waveform undergoes no further change.

81. The apparatus of claim 80, wherein said appearance of said plethysmographic waveform is indicative of systolic pressure of said pulsatile vascular compartment, said maximum signal intensity of said plethysmographic signal is indicative of mean pressure of said pulsatile vascular compartment, and said point at which said plethysmographic waveform ceases to change is indicative of diastolic pressure of said pulsatile vascular compartment.

82. The apparatus of claim 81, wherein said means for selectively occluding comprises a cuff disposed about said patient body portion and inflatable to a pressure sufficient to occlude said pulsatile vascular compartment, and said indication of said systolic, mean and diastolic pressure of said pulsatile vascular compartment is correlated to the actual systolic, mean and diastolic pressures of said vascular compartment by pressure transducer means associated with said cuff.

83. A method of compensating for non-homogeneous blood flow in a pulsatile vascular compartment of a patient body portion to enhance the accuracy of detection of a blood-related parameter at said patient body portion, comprising:

applying electrical current signals having selected frequencies across at least a portion of said body portion; and occluding said pulsatile vascular compartment during at least a portion of the cardiac cycle of said patient while detecting said blood-related parameter while said electrical current signals are applied.

84. The method of claim 83, wherein said occlusion further comprises application of pressure to said pulsatile vascular compartment in the region of the mean pressure thereof.

85. A method of compensating for non-homogeneous blood flow in a pulsatile vascular compartment of a patient body portion to enhance the accuracy of detection of a blood-related parameter at said patient body portion, said patient body portion also including a non-pulsatile vascular compartment, said method comprising:

applying electrical current signals having selected frequencies across at least a portion of said body portion; and applying pressure to said patient body portion sufficient to occlude said non-pulsatile vascular compartment while permitting blood flow through said pulsatile vascular compartment and detecting said blood-related parameter while said electrical current signals are applied.

* * * * *